United States Patent
Setlur et al.

(10) Patent No.: US 9,129,350 B2
(45) Date of Patent: Sep. 8, 2015

(54) SYSTEMS AND METHODS TO ANALYZE AN IMMUNOASSAY TEST STRIP COMB MEMBER

(75) Inventors: Pradeep Setlur, Carmel, IN (US); Kerrm Yau, Carmel, IN (US); Sandra Toledo, West Lafayette, IN (US); Jason Richardson, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 360 days.

(21) Appl. No.: 13/807,928

(22) PCT Filed: Jul. 19, 2011

(86) PCT No.: PCT/US2011/044471
§ 371 (c)(1),
(2), (4) Date: May 15, 2013

(87) PCT Pub. No.: WO2012/012382
PCT Pub. Date: Jan. 26, 2012

(65) Prior Publication Data
US 2013/0222634 A1      Aug. 29, 2013

Related U.S. Application Data

(60) Provisional application No. 61/366,063, filed on Jul. 20, 2010, provisional application No. 61/415,211, filed on Nov. 18, 2010, provisional application No. 61/441,220, filed on Feb. 9, 2011.

(51) Int. Cl.
*G06K 9/00* (2006.01)
*G01N 31/22* (2006.01)
(Continued)

(52) U.S. Cl.
CPC .......... *G06T 7/0002* (2013.01); *G01N 21/8483* (2013.01); *G06T 7/0012* (2013.01);
(Continued)

(58) Field of Classification Search
CPC ....... G06T 7/00; G06T 7/0002; G06T 7/0012; G06T 7/408; G06T 2207/10024; G01N 2021/845; G01N 2021/8466; G06F 19/00; G06F 19/3418
USPC .......... 382/100, 110, 128, 159, 191, 190, 155, 382/162, 168, 173, 181, 232, 254, 276, 309, 382/312, 325; 422/430
See application file for complete search history.

(56) References Cited

U.S. PATENT DOCUMENTS 4,822,565 A * 4/1989 Kohler .......................... 422/425
4,847,487 A   7/1989 Bordini
(Continued)

FOREIGN PATENT DOCUMENTS

JP   63-162448 A   7/1988
JP   07190940 A   7/1995
(Continued)

OTHER PUBLICATIONS

Examination Report mailed Feb. 10, 2015 from the Japanese Patent Office in related Japanese Patent Application No. 2013-520795.
(Continued)

*Primary Examiner* — Sheela Chawan
(74) *Attorney, Agent, or Firm* — C.W. Arnett; Faegre Baker Daniels LLP

(57) ABSTRACT

Systems and methods for analyzing test strip comb members having a plurality of fingers are disclosed. The systems and methods may analyze a test strip comb member to determine the presence of one more analytes on each of the plurality of fingers.

30 Claims, 29 Drawing Sheets

(51) Int. Cl.
  *G06T 7/00*   (2006.01)
  *G01N 21/84*  (2006.01)
  *G06T 7/40*   (2006.01)

(52) U.S. Cl.
  CPC ......... *G06T 7/408* (2013.01); *G01N 2021/845* (2013.01); *G01N 2021/8466* (2013.01); *G06T 2207/10024* (2013.01)

(56) References Cited

U.S. PATENT DOCUMENTS

| | | | |
|---|---|---|---|
| 6,014,451 A * | 1/2000 | Berry et al. | 382/110 |
| 6,372,515 B1 | 4/2002 | Casterlin et al. | |
| 6,535,624 B1 * | 3/2003 | Taylor, Jr. | 382/128 |
| 6,646,264 B1 | 11/2003 | Modiano et al. | |
| 7,354,721 B2 * | 4/2008 | Tchaga | 435/7.1 |
| 8,189,901 B2 | 5/2012 | Modiano et al. | |
| 2005/0251347 A1 | 11/2005 | Perona et al. | |
| 2006/0112628 A1 | 6/2006 | Kotyk et al. | |
| 2006/0198765 A1 * | 9/2006 | Gjerde et al. | 422/102 |
| 2007/0161103 A1 | 7/2007 | Buchmann et al. | |
| 2011/0019883 A1 | 1/2011 | Bremnes et al. | |
| 2011/0042213 A1 * | 2/2011 | Updyke et al. | 204/461 |
| 2011/0042217 A1 * | 2/2011 | Updyke et al. | 204/620 |

FOREIGN PATENT DOCUMENTS

| | | |
|---|---|---|
| JP | 10-327301 | 12/1998 |
| JP | 10-332691 | 12/1998 |
| JP | 2000-338106 A | 12/2000 |
| JP | 2001-305148 A | 10/2001 |
| JP | 2003043049 A | 2/2003 |
| JP | 2004-321090 A | 11/2004 |
| JP | 2007-47038 A | 2/2007 |
| JP | 2007127465 A | 5/2007 |
| JP | 2007212261 A | 8/2007 |
| JP | 2007523335 A | 8/2007 |
| JP | 2008014680 A | 1/2008 |
| JP | 2009244232 A | 10/2009 |
| WO | WO2008/108328 A1 | 9/2008 |
| WO | WO2009/022003 A1 | 2/2009 |

OTHER PUBLICATIONS

English Translation of the Chinese Office Action mailed Nov. 26, 2014 and the Search Report.
International Search Report and Written Opinion in PCT/US2011/44471, Dec. 7, 2011, 8 pgs.
Envirologix™ QuickStix™ Reader Quick Guide, Doc. M82,0907 (2010), 1 pg.
Envirologix™ QuickGuide for QuickScan, Doc. M44-0710 (2010), 1 pg.
Skannex™ Lateral Flow and Elisa Reader Systems, www.skanex.com (2010), 2 pgs.
Handheld >> Diagnostic Consulting Network web pages, www.dcndx.com/products/readers/handheld, Dec. 13, 2010, 2 pgs.
Benchtop >> Diagnostic Consulting Network web pages, www.dcndx.com/products/readers/benchtop, Dec. 13, 2010, 3 pgs.
Visualizer >> Diagnostic Consulting Network web pages, www.dcndx.com/products/readers/visualizer, Dec. 13, 2010, 2 pgs.
Detekt Biomedical L.L.C., Colorimetric and Fluorescent Lateral flow Strip Reader Imaging Systems webpage, www.idetekt.com/web2/technology.htm, Dec. 13, 2010, 1 pg.
Qiagen, ESEQuant Lateral Flow System, Technical Information, Nov. 2010, 4 pgs.
Fangi et al., Photointerpretation and Small Scale Stereoplotting with Digitally Rectified Photographs with Geometrical Constraints, University of Ancona, via Brecce Bianche, 2001, 8 pgs.

* cited by examiner ical stage patent application
SYSTEMS AND METHODS TO ANALYZE AN IMMUNOASSAY TEST STRIP COMB MEMBER

CROSS REFERENCE TO RELATED APPLICATION

This application is a U.S. national stage patent application of PCT/US2011/044471, filed Jul. 19, 2011, which claims priority to U.S. Provisional Application Ser. No. 61/366,063, filed Jul. 20, 2010, U.S. Provisional Application Ser. No. 61/415,211, filed Nov.18, 2010, and U.S. Provisional Application Ser. No. 61/441,220, filed Feb. 9, 2011, the disclosures of which are expressly incorporated by reference herein

FIELD

The present invention relates to methods and apparatus for analysis of a plurality of test strips and in particular to the analysis of a plurality of test strips for identifying the presence or absence of various proteins of interest in plant material.

BACKGROUND

Lateral flow immunoassay ("IA") test strips have been validated to rapidly and selectively detect analytes of interest, such as proteins, in plant material, such as corn leaf samples. Exemplary IA lateral flow strips are available from Agdia located at 30380 County Road 6 in Elkhart, Ind. 46514.

Manual methods have been used in the past to read IA lateral flow strips. The process begins with the receipt of sample tubes that are in a 12×8 matrix test stand. The sample tubes include plant material. The sample tubes are placed in a robotic system to read and store individual barcode information from the sample tubes. The samples are then processed (bead addition, buffer addition, capping tubes, grinding and de-capping tubes) to extract plant proteins. Subsequently, a 12 strip IA lateral flow strip comb has one finger or strip inserted into each sample in a given row. For a 12×8 matrix, eight 12 strip combs are needed.

The fingers of the IA strips are designed to provide a colored band a given location on the finger if the protein is present in plant sample. Each finger may include multiple potential bands at spaced apart locations, each of which being associated with a different protein. As such, a finger may be used to test for the presence of multiple proteins in the plant sample.

By way of example, a finger has a first location whereat a colored band will appear if a first protein is present in the plant sample the finger is exposed to and a second location whereat a colored band will appear if a second protein is present in the plant sample the finger is exposed to. Assuming the finger is exposed to a plant sample containing both the first protein and the second protein, a colored band is provided at both the first location and the second location. Assuming the finger is exposed to a plant sample containing neither the first protein or the second protein, no colored band is provided at either the first location or the second location. Assuming the finger is exposed to a plant sample containing the first protein but not the second protein, a colored band is provided at the first location but not the second location. Assuming the finger is exposed to a plant sample containing the second protein but not the first protein, a colored band is provided at the second location but not the first location.

After a five minute incubation, the combs are removed from the samples and manually read to determine the presence of one or more proteins in the respective samples. For the example above, an operator examines the fingers to see if a band is present at the first location or the second location. The presence or absence of a band is manually entered into a computer program that merges the information with the barcode information stored earlier. The combs may then be discarded.

SUMMARY

In an exemplary embodiment of the present disclosure, a method of analyzing test strips is provided. In another exemplary embodiment of the present disclosure, a system for analyzing test strips is provided. In a further exemplary embodiment, a computer readable medium is provided including instructions which when executed by an electronic controller analysis test strips.

In an exemplary embodiment of the present disclosure, a method of analyzing a test strip comb member having a plurality of spaced-apart fingers is provided. Each of the fingers having been exposed to a respective plant material. Each of the fingers being configured to indicate the presence of one or more plant analytes in the respective plant material. The method comprising capturing an electronic image of the plurality of fingers of the test strip comb member; and analyzing the electronic image with an electronic controller to determine if for a first finger of the test strip comb member a first plant analyte is present and for a second finger of the test strip comb member if a second plant analyte is present.

In an example thereof, the first plant analyte is the same as the second plant analyte. In another example thereof, the step of capturing the electronic image of the plurality of fingers of the test strip comb member includes the steps of monitoring a field of view of a camera; detecting a presence of the test strip comb member in the field of view of the camera; and storing the electronic image of the plurality of fingers of the test strip comb on a computer readable medium when the test strip comb member is detected in the field of view of the camera. In one variation thereof the step of detecting the presence of the test strip comb member in the field of view of the camera includes the steps of capturing a frame of the camera; and analyzing a portion of the captured frame to determine the presence of the test strip comb member. In a further variation thereof, the step of analyzing the portion of the captured frame to determine the presence of the test strip comb member includes the steps of determining an average pixel brightness value for the portion of the captured frame; comparing the average pixel brightness value to a first threshold value; determining a number of pixels of the portion of the captured frame whose brightness value exceeds the average brightness value; comparing the number of pixels of the portion of the captured frame to a second threshold; determining the presence of the test strip comb member when the average pixel brightness exceeds the first threshold and the number of pixels of the portion of the captured frame exceeds the second threshold; and storing the captured frame as the electronic image on a computer readable medium.

In yet another example, the electronic image is a color image, each pixel of the color image having a plurality of color values, and the step of analyzing the electronic image with the electronic controller to determine if for the first finger of the test strip comb member the first plant analyte is present and for the second finger of the test strip comb member if the second plant analyte is present includes the steps of analyzing a first portion of the electronic image corresponding to the first finger; determining based on at least one color value of the first portion whether the first plant analyte is bound to the first finger; analyzing a second portion of the electronic image corresponding to the second finger; and determining based on at least one color value of the second portion whether the second plant analyte is bound to the second finger. In a variation thereof, the step of determining based on at least one color value of the first portion whether the first plant analyte is bound to the first finger includes the steps of for each pixel of the first portion comparing a first color value to a first threshold; comparing a second color value to a second threshold; classifying the pixel as one of indicative of the first analyte being present and indicative of the first analyte being absent based on the comparison of the first color value to the first threshold and the comparison of the second color value to the second threshold; determining based on a number of the pixels classified as being indicative of the first analyte being present whether the first analyte is bound to the first finger; and the step of determining based on at least one color value of the second portion whether the second plant analyte is bound to the second finger includes the steps of for each pixel of the second portion comparing a first color value to a first threshold; comparing a second color value to a second threshold; classifying the pixel as one of indicative of the second analyte being present and indicative of the second analyte being absent based on the comparison of the first color value to the first threshold and the comparison of the second color value to the second threshold; determining based on a number of the pixels classified as being indicative of the second analyte being present whether the second analyte is bound to the second finger.

In still another example thereof, the method further comprises the step of removing a green bias from the electronic image due to excess plant material in the electronic image. In a further example thereof, the method further comprises the step of removing a red bias from the electronic image due to dirt in the electronic image.

In a yet further example thereof, the electronic image is a color image, each pixel of the color image having a plurality of color values, and the method further comprising the step of color equalizing the electronic image. In a variation thereof, the step of color equalizing the electronic image includes the steps of identifying a respective region of interest for each finger; color equalizing the respective region of interest of the first finger; and color equalizing the respective region of interest of the second finger independent of the first finger. In a further variation thereof, the step of color equalizing the respective region of interest of the first finger includes the steps of scaling a first color value for each pixel of the respective region of interest of the first finger so that the average first color value of all of the pixels of the respective region of interest of the first finger equals a first value; and scaling a second color value for each pixel of the respective region of interest of the first finger so that the average second color value of all of the pixels of the respective region of interest of the first finger equals a second value. In yet a further variation thereof, the first value is equal to the second value.

In still yet a further example thereof, the plurality of fingers each include a respective region of interest which includes a plurality of spaced apart band locations and the step of analyzing the electronic image with the electronic controller to determine if for the first finger of the test strip comb member the first plant analyte is present and for the second finger of the test strip comb member if the second plant analyte is present includes the steps of locating the respective region of interest in the electronic image for the first finger and the second finger; thresholding the image based on at least one average background intensity of the electronic image; and segmenting the electronic image to remove small blobs. In a variation thereof, the step of locating the respective region of interest in the electronic image for the first finger and the second finger includes the steps of determining an orientation of the test strip comb member in the electronic image; deskewing the image such that the first finger and the second finger of the test strip comb member are vertically oriented; locating a first reference in the electronic image for the first finger, the first region of interest of the first finger being at a first known position relative to the first reference; and locating a second reference in the electronic image for the second finger, the second region of interest of the second finger being at a second known position relative to the second reference. In a further variation thereof, the step of locating the respective region of interest in the electronic image for the first finger and the second finger further includes the step of correcting the electronic image for perspective distortion. In yet a further variation thereof, the step of locating the respective region of interest in the electronic image for the first finger and the second finger further includes the step of determining a scaling factor for the electronic image. In still a further variation, the step of thresholding the image based on at least one average background intensity includes the steps of determining an average background intensity for a first color value; determining an average background intensity for a second color value; for each pixel, if one of a value of the pixel for the first color value exceeds the average background intensity for the first color value and a value of the pixel for the second color value exceeds the average background intensity for the second color value then assigning the pixel a third color and otherwise assigning the pixel a fourth color.

In still yet a further example thereof, the method comprises the step of storing a qualitative indication of a determination of the presence of the first analyte and a qualitative indication of a determination of the presence of the second analyte. In still another example thereof, the method comprises the step of storing a quantitative indication of a determination of an expression level of the first analyte and a quantitative indication of a determination of an expression level of the second analyte. In yet still another example thereof, the method comprises the step of providing a closed structure having an opening in a top adapted to permit the test strip comb member to enter an interior of the closed structure and an opening in a bottom adapted to permit the test strip comb member to exit the interior of the closed structure, wherein the step of capturing the electronic image of the plurality of fingers of the test strip comb member occurs while the test strip comb member is positioned in the interior of the closed structure.

In another exemplary embodiment of the present disclosure, a system for analyzing a test strip comb having a plurality of spaced-apart fingers is provided. Each of the fingers having been exposed to a respective plant material. Each of the fingers being configured to indicate the presence of one or more plant analytes in the respective plant material. The system comprising a camera; a background member, the test strip comb member being within a field of view of the camera and in front of the background member; a light source providing generally uniform illumination of the field of view of the camera; and an electronic controller operatively coupled to the camera and configured to analyze an electronic image of the plurality of fingers of the test strip comb member to determine if for a first finger of the test strip comb member a first plant analyte is present and for a second finger of the test strip comb member if a second plant analyte is present.

In an example thereof, the system further comprises a closed structure having an opening in a top adapted to permit the test strip comb member to enter an interior of the closed structure and an opening in a bottom adapted to permit the test strip comb member to exit the interior of the closed structure, the electronic image of the plurality of fingers of the test strip comb member being captured while the test strip comb member is positioned in the interior of the closed structure. In a variation thereof, the background member is a removable plate which provides a contrasting background relative to the test strip comb member.

In another example thereof, the system further comprises a conveyor system having a transport member upon which the test strip comb member is supported, wherein the electronic controller is operatively coupled to a drive system of the conveyor system. In a variation thereof, the background member is the transport member of the conveyor system. In another variation thereof, the system further comprises a cleaning system to remove excess plant debris from the transport member. In yet another variation thereof, the system further comprises a feeder system which places the test strip comb member on the conveyor system. In a further variation thereof, the feeder system places the test strip comb member onto transport member with a generally uniform spacing relative to a prior test strip comb member and a subsequent test strip comb member.

In another example, the system further comprises a display device which displays a user interface comprising a first region which displays the electronic image of the test strip comb member; a second region which displays an indicator providing an indication to the operator of when the electronic controller is ready to analyze a second test strip comb member. In a variation thereof, a set number of test strip comb members are to be analyzed and the user interface provides an indication with the display device of a number of test strip members that have been analyzed.

The above and other features of the present disclosure, which alone or in any combination may comprise patentable subject matter, will become apparent from the following description and the attached drawings.

BRIEF DESCRIPTION OF THE DRAWINGS

The detailed description particularly refers to the following figures, in which.

Corresponding reference characters indicate corresponding parts throughout the several views.

DETAILED DESCRIPTION OF THE DRAWINGS

The embodiments disclosed below are not intended to be exhaustive or to limit the invention to the precise forms disclosed in the following detailed description. Rather, the embodiments are chosen and described so that others skilled in the art may utilize their teachings. While the present disclosure is primarily directed to the analysis of plant material contained in a plurality of test tubes, it should be understood that the features disclosed herein may have application to analysis of other materials contained in a plurality of test tubes or other containers.

Figure 1:
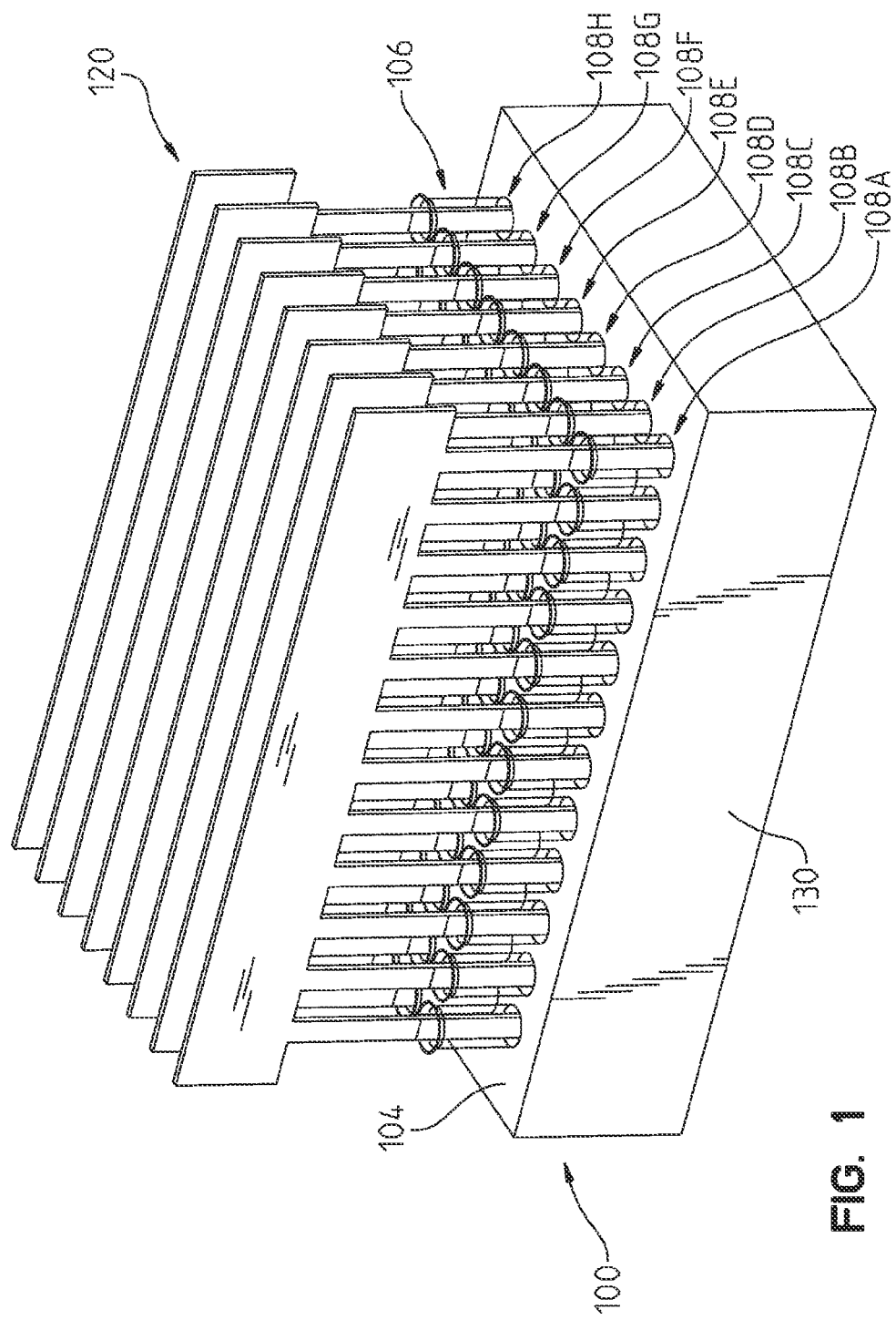
FIG. 1 illustrates a perspective view of an exemplary test tube stand holding a plurality of test tubes in a plurality of rows, each test tube having a test strip inserted into an open end of the test tube.
Figure 2:
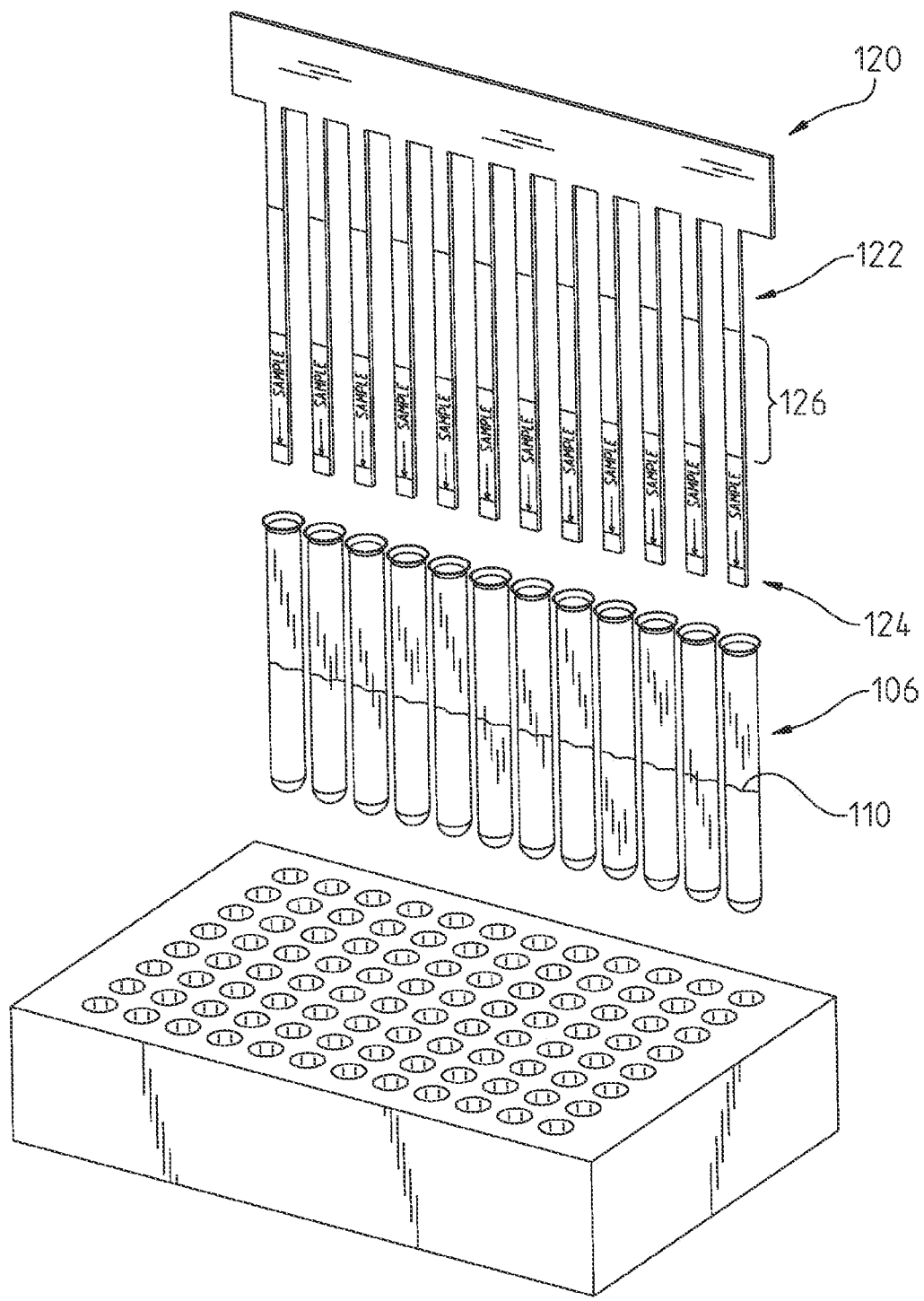
FIG. 2 illustrates the assembly of a first row of test tubes to the test stand of FIG. 1 and the assembly of a first test strip comb member to the first row of test tubes.

Referring to FIGS. 1 and 2, an exemplary test tube stand 100 is shown. Test tube stand 100 includes a plurality of recesses 102 provided in an upper surface 104 of test tube stand 100. A test tube 106 may be inserted into each of these recesses 102 and held in a generally vertical manner. The test tubes 106 are arranged generally in rows 108A-H. In the illustrated embodiment, test tube stand 100 includes recesses to hold eight rows 108 of test tubes 106; each row 108 includes twelve test tubes 106. Exemplary analytes may be tested for a plurality of applications. Exemplary applications include drug testing, pharmaceutical testing, DNA testing, and other types of testing.

Each test tube 106 includes a substance 110 to be analyzed. In one embodiment, the substance 110 is generally a liquid with materials provided therein. Exemplary materials include proteins and other types of analytes. In one embodiment, substance 110 is generally a liquid with plant material provided therein. Exemplary plant material includes proteins and other types of analytes.

Figure 3:
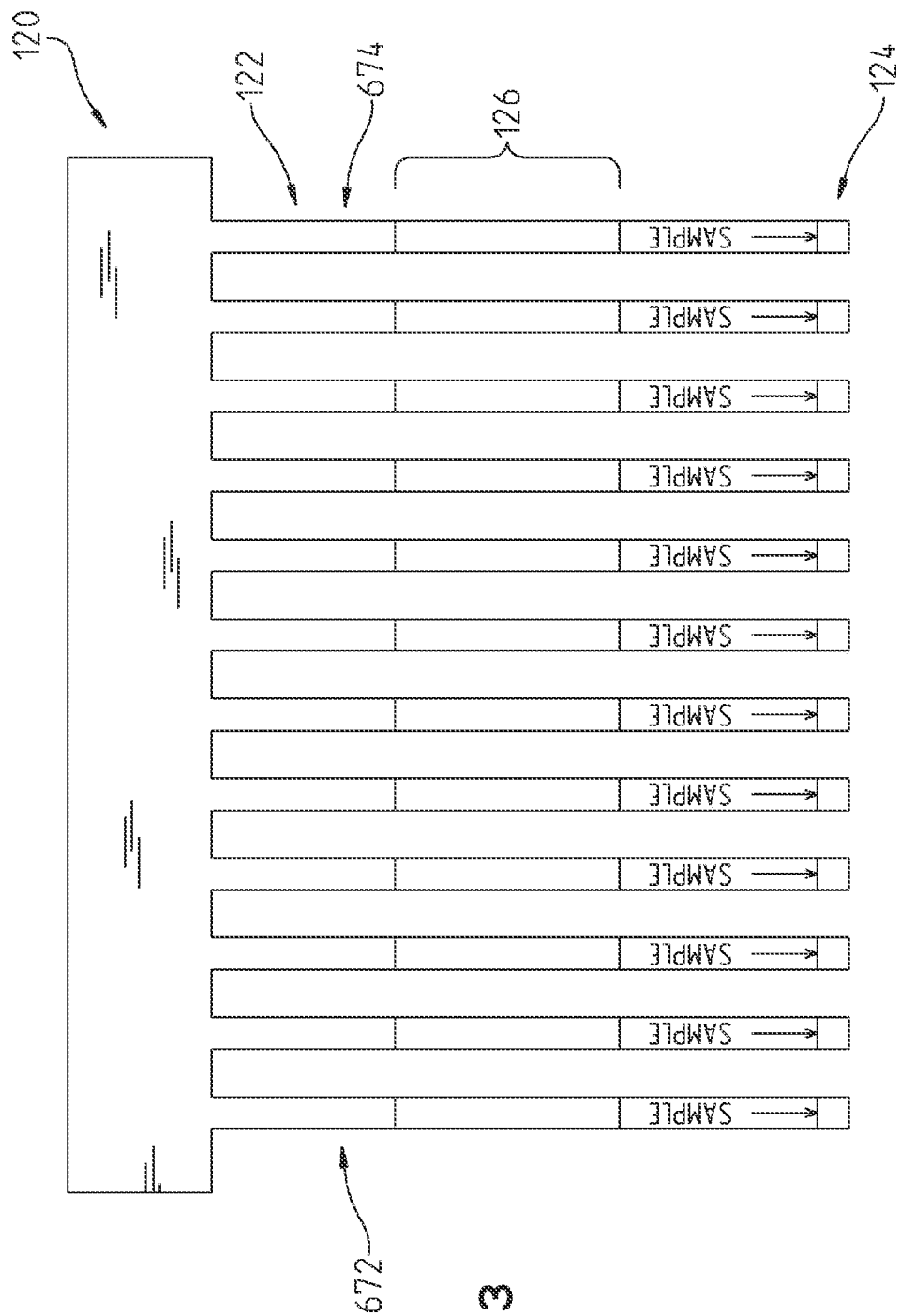
FIG. 3 illustrates a front view of a first test strip comb member.
Figure 3A:
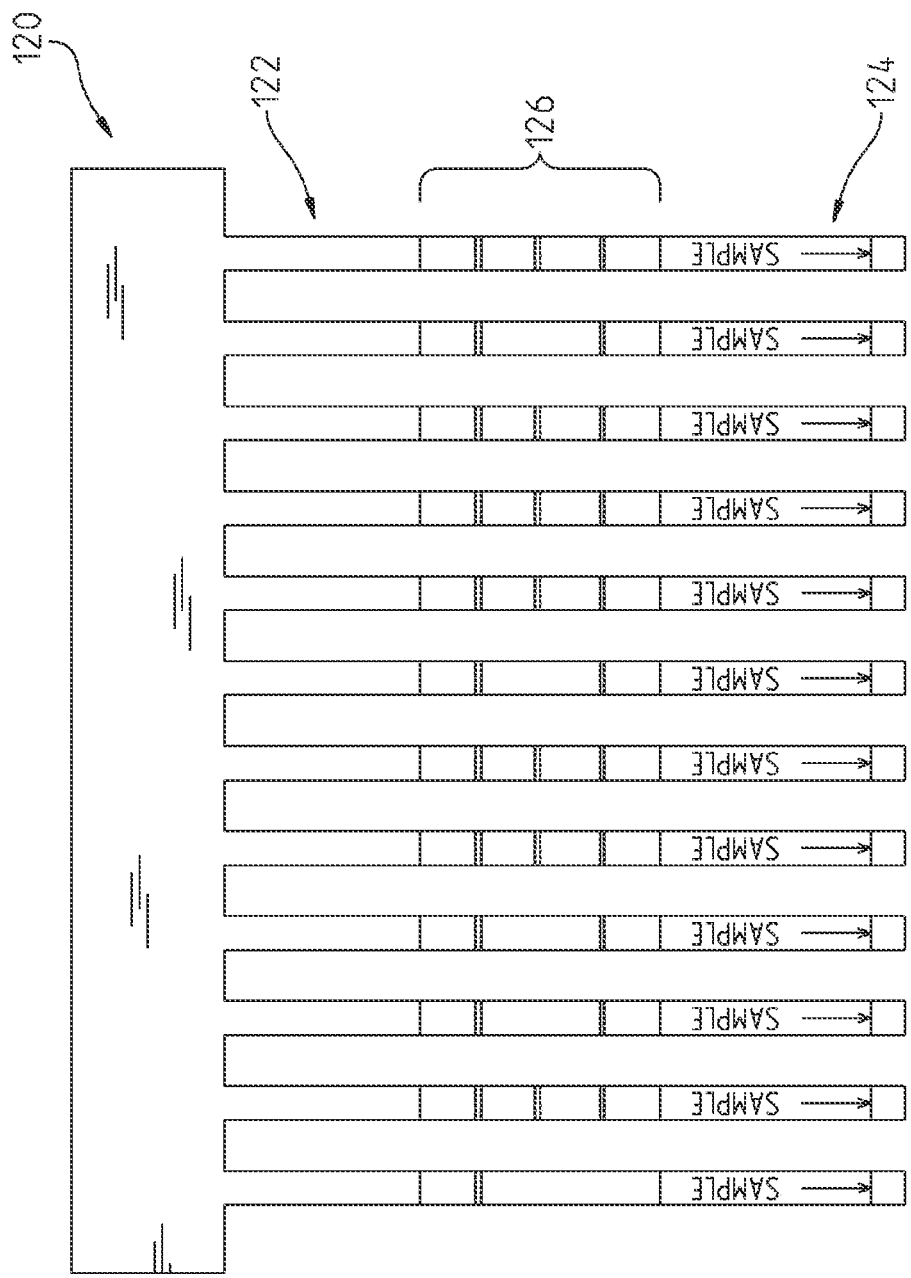
FIG. 3A is an image of a first test strip comb member.

A test strip comb member 120 is used to detect the presence or absence of materials within a substance 110 in a test tube 106, such as proteins. Test strip comb member 120 includes a plurality of fingers 122 having a lower portion 124 which are inserted into the open end of test tube 106 and into the substance 110 within test tube 106. Each of the fingers 122 also includes a second region 126 wherein colored bands (see FIG. 3A) illustrate the presence of a material in the substance 110 into which the respective finger was inserted. In one embodiment, the intensity of the color of a given band provides a measure of the concentration of the material in the substance 110. In one example, wherein the color band is red, a darker red indicates a higher concentration of the material in substance 110. As illustrated in FIG. 2, test strip comb member 120 includes twelve fingers 122, one for each of the test tubes 106 in a given row 108. In one embodiment, test strip comb member 120 includes fewer fingers than the number of test tubes in a row. In this case, multiple test strip comb members 120 are used to cover a given row 108. An exemplary test strip comb member 120 is the IA lateral flow strip available from Agdia located at 30380 County Road 6 in Elkhart, Ind. 46514. The IA lateral flow strip has been validated to rapidly and selectively detect proteins of interest in plant material, such as corn leaf samples.

In one embodiment, the plant material is placed in a test tube. The test tube includes identification information regarding the plant material in the tube. In one embodiment, this identification information is tied to a bar code supported by the test tube. The individual test tubes are assembled into a test tube stand 100 which also may include identification information regarding the test tubes supported thereby and their locations. In one embodiment, this identification information regarding the test tubes is tied to a bar code 130 provided on test tube stand 100.

The plant material in the test tubes is then processed to extract plant proteins. Exemplary processing includes one or more of bead addition, buffer addition, capping tubes, grinding, and de-capping tubes. Subsequently, fingers 122 of test strip comb member 120 are placed in the respective tubes 106. After an incubation time, the test strip comb members 120 are individually removed from the tubes 106 and analyzed to determine the presence of one or more proteins by looking for the presence of a band at pre-determined locations in the second region 126 of the fingers 122. In one embodiment, a level of protein expression is also detected. An exemplary incubation time is about 5 minutes. Although the illustrated embodiment discusses the analysis of a comb member, the methods and processing sequences disclosed herein may be used for a single strip.

Figure 4:
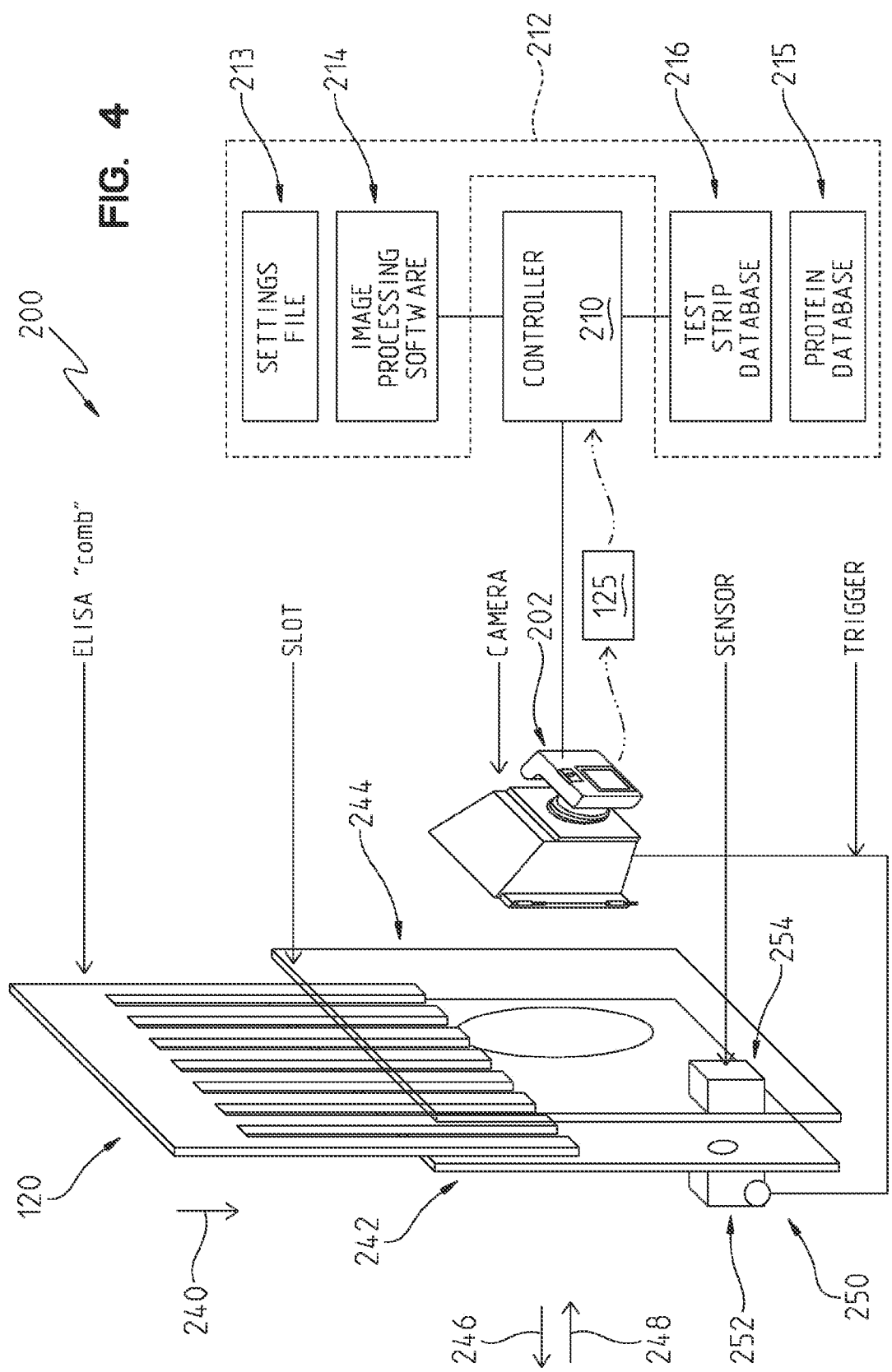
FIG. 4 illustrates a system for analyzing the first test strip comb member of FIG. 3.

Referring to FIG. 4, an exemplary system 200 for analyzing the second region 126 of the fingers 122 of a test strip comb member 120 is shown. In one embodiment, system 200 further analyzes the second region 126 to determine a level of protein expression. System 200 includes a camera 202 which captures an image 124 of test strip comb member 120. In one embodiment, camera 202 is a color camera which captures an electronic image of test strip comb member 120. The electronic image contains a plurality of rows of pixels each of which have their own values. Each pixel includes a first value corresponding to the amount of red seen at that image location, a second value corresponding to the amount of green seen at that image location, and a third value corresponding to the amount of blue seen at that image location. In alternative embodiments, different color values may be determined by camera 202. The captured image 124 is provided to a controller 210 which analyzes the image to determine the presence of one or more proteins in the various substances 110 of the various test tubes 106. In one embodiment, system 200 further analyzes the second region 126 to determine a level of protein expression. In one embodiment, controller 210 is a desktop computer, a laptop computer, a handheld computing device, or other device which may be programmed.

Figure 5:
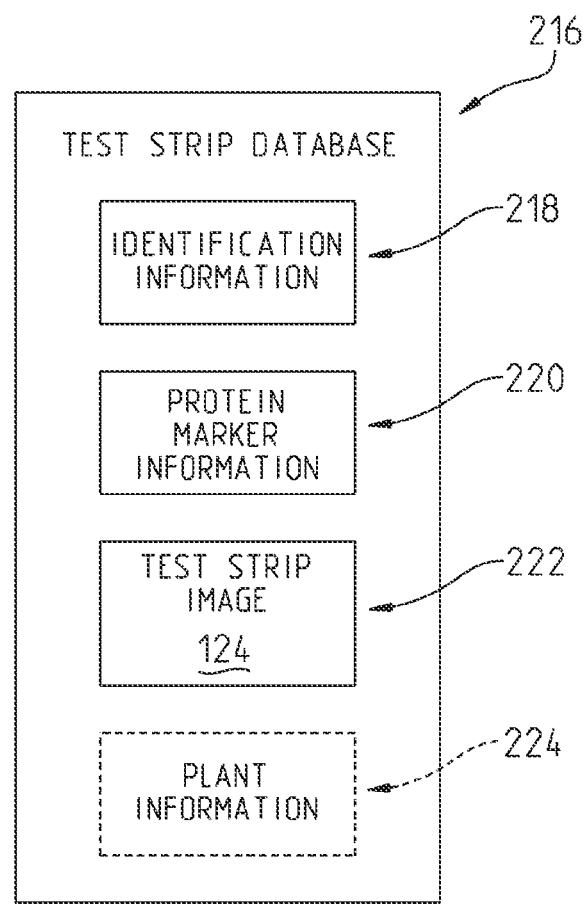
FIG. 5 illustrates the information in a exemplary database of the system of FIG. 4.

A memory 212 accessible by controller 210 includes image processing software 214 which may be executed by controller 210 to analyze the image 124. Memory 212 further includes a test strip database 216 which records the information determined from lower portion 124 by controller 210. Referring to FIG. 5, an exemplary representation of test strip database 216 is illustrated. Test strip database 216 includes identification information 218, protein marker information 220, image information 222 such as a copy of the image 124 that was analyzed or identification of the filename of the image 124, and plant information 224. Plant information 224 may include information regarding the plant that the substance in a given test tube was taken from. The identification information 218 may be the bar code information for the test tube, bar code information for the test tube stand, the test tube location in the test tube stand, and other information which identifies the test tube or test tube stand. In one embodiment, identification information is a barcode or other identifying indicia on the comb member 122. As explained herein, in one embodiment, the protein marker information is simply an indication of the presence or absence of one or more proteins. In another embodiment, the protein marker information is both an indication of the presence or absence of one or more proteins and a level of expression for at least one of the proteins.

Memory 212 is associated with one or more processors of controller 210 and may include, but is not limited to, memory associated with the execution of software and memory associated with the storage of data. Memory 212 may be any available computer readable media that may be accessed by one or more processors of controller 210 and includes both volatile and non-volatile media. Further, computer readable-media may be one or both of removable and non-removable media. By way of example, computer-readable media may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by controller 210. Memory 212 may be multiple memories accessible by one or more processors of controller 210.

Returning to FIG. 4, a test strip comb member 120 passes in direction 240 between a first plate 242 and a second plate 244. The space between plates 242 and 244 defines a slot. In one embodiment, first plate 242 is selected to have optical properties to provide a contrasting background to test strip comb member 120. In one embodiment, first plate 242 is generally black in color. In one embodiment, second plate 244 is selected to permit test strip comb member 120 to be visible to camera 202. In one embodiment, second plate 244 is generally transparent.

The optics of camera 202 focus the image plane of camera 202 at the slot provided between first plate 242 and second plate 244. In one embodiment, second plate 244 is not included. In this case, the camera 202 is focused on the region in front of the first plate 242 where test strip comb member 120 is presented. The closeness of first plate 242 and second plate 244 generally prevents test strip comb member 120 from folding in directions 246 and 248. A sensor 250 is provided which monitors the region in front of first plate 242 and when second plate 244 is included behind second plate 244. The sensor provides an indication to controller 210 of when test strip comb member 120 is within or going to be within the field of view of camera 202. Controller 210 based on the indication from sensor 250 controls camera 202 to take an image 124 of test strip comb member 120. In one embodiment, sensor 250 is an optical sensor which detects when test strip comb member 120 interrupts a beam of optical energy passing from a source 252 to a detector 254. In the illustrated embodiment, sensor 250 is coupled to camera 202 directly and camera 202 determines when to capture image 124. In one embodiment, sensor 250 is provided in software. An exemplary sensor in software is a processing sequence which monitors a region of an image, such as a row, and analyzes a measure of that region to determine a presence or absence of a comb member 122. In one embodiment, the test strip member 120 falls out of a lower edge of the slot between first plate 242 and second plate 244 into a discard container.

Figure 12:
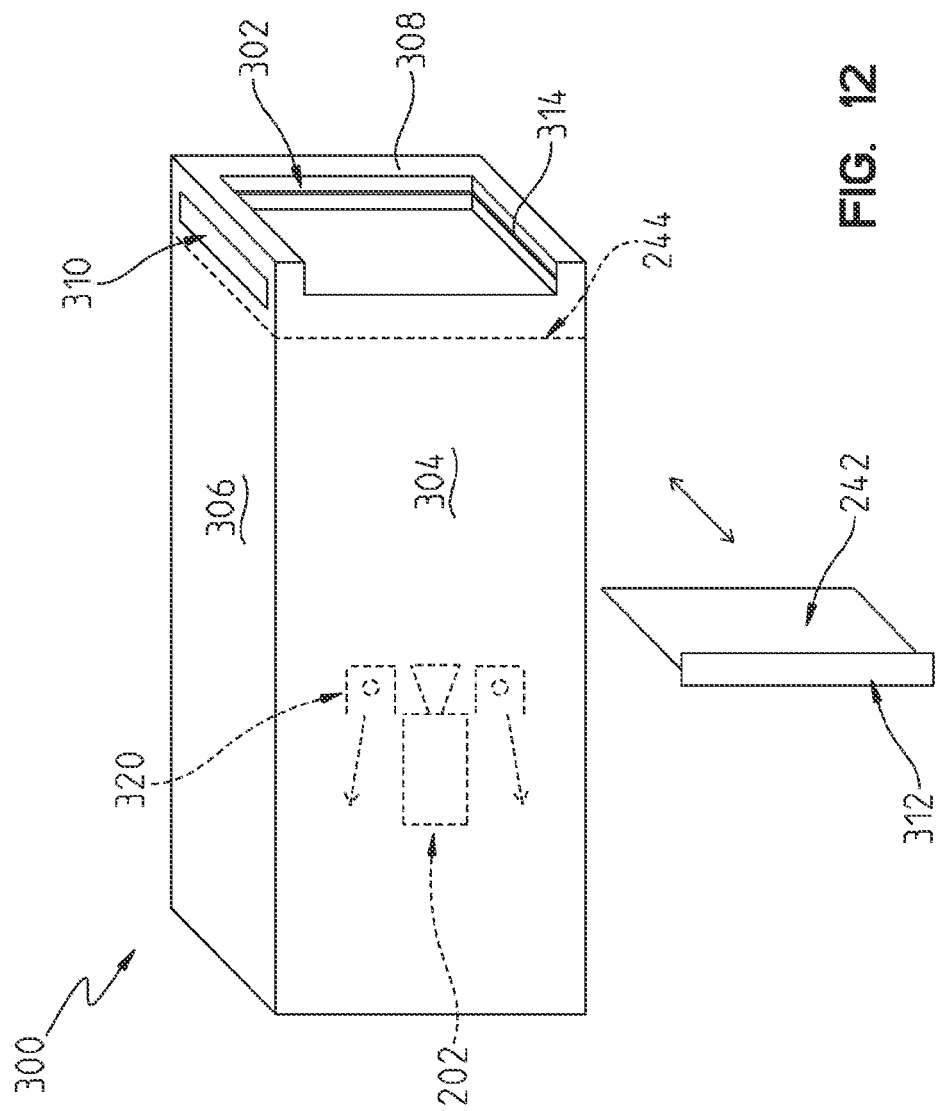
FIG. 12 illustrates an exemplary system for analyzing the first test strip comb member of FIG. 3.

Referring to FIG. 12, an exemplary reading device 300 is shown. Reading device 300 includes a frame 302 supporting a plurality of walls, walls 304, 306, and 308 being shown. Walls 304 and 306 and the remainder of the walls are generally opaque. Positioned within reading device 300 is camera 202 which is directed at the slot 310. Slot 310 is provided between a first plate 242 and camera 202. In one embodiment, a second plate 244 is included and slot 310 is between first plate 242 and second plate 244. In the illustrated embodiment, first plate 242 includes a handle 312 and is removably coupled to the remainder of reading device 300. First plate 242, in the illustrated embodiment, is received by guides 314 provided in frame 302 and generally forms an end wall of reading device 300.

In operation, a test strip comb member 120 is dropped through slot 310 in front of first plate 242. Sensor 250 determines the presence of test strip comb member 120 and camera 202 captures an image of test strip comb member 120. The test strip comb member 120 then falls out of an open bottom portion of reading device 300 into a container.

By having first plate 242 being removable, a first first plate 242 may be removed and replaced with a second first plate 242 once the first first plate 242 becomes soiled with plant material. In one embodiment, both first plate 242 and second plate 244, when provided, may be removable from the remainder of reading device 300.

In one embodiment, controller 210 provides an indication to an operator of when first plate 242 should be changed or cleaned. Exemplary indications include a prompt on a monitor, a light, other visual cues, an audio cue, a tactile cue, or combinations thereof. The controller 210 determines when to provide the indication in response to an analysis of the amount of plant material on first plate 242 by the software being executed by controller 210.

In one embodiment, a light source 320 is provided to illuminate the region in front of first plate 242. In one embodiment, the type of light source and its location are chosen to provide uniform, soft light on the test strip comb member 120. In the illustrated embodiment, light source 320 is a ring light which is placed around the lens of camera 202. Light source 320 is facing away from first plate 242 such that the light produced by light source 320 must first be reflected from one or more of the walls of reading device 300 to reach first plate 242. This arrangement provides more even lighting of the region between first plate 242 and second plate 244 than having light source 320 face towards second plate 244. In one embodiment, light source 320 is oriented about ninety degrees to first plate 242 and positioned along a side wall of reading device 300.

As explained in more detail herein, image processing techniques are used to "read" the test strip comb member 120. For each finger 122, a determination is made whether a given analyte, such as a protein, is present or absent. Exemplary analytes include proteins, portions of DNA, and other suitable analytes. This information is collated with the identification information for the test tube.

Figure 6:
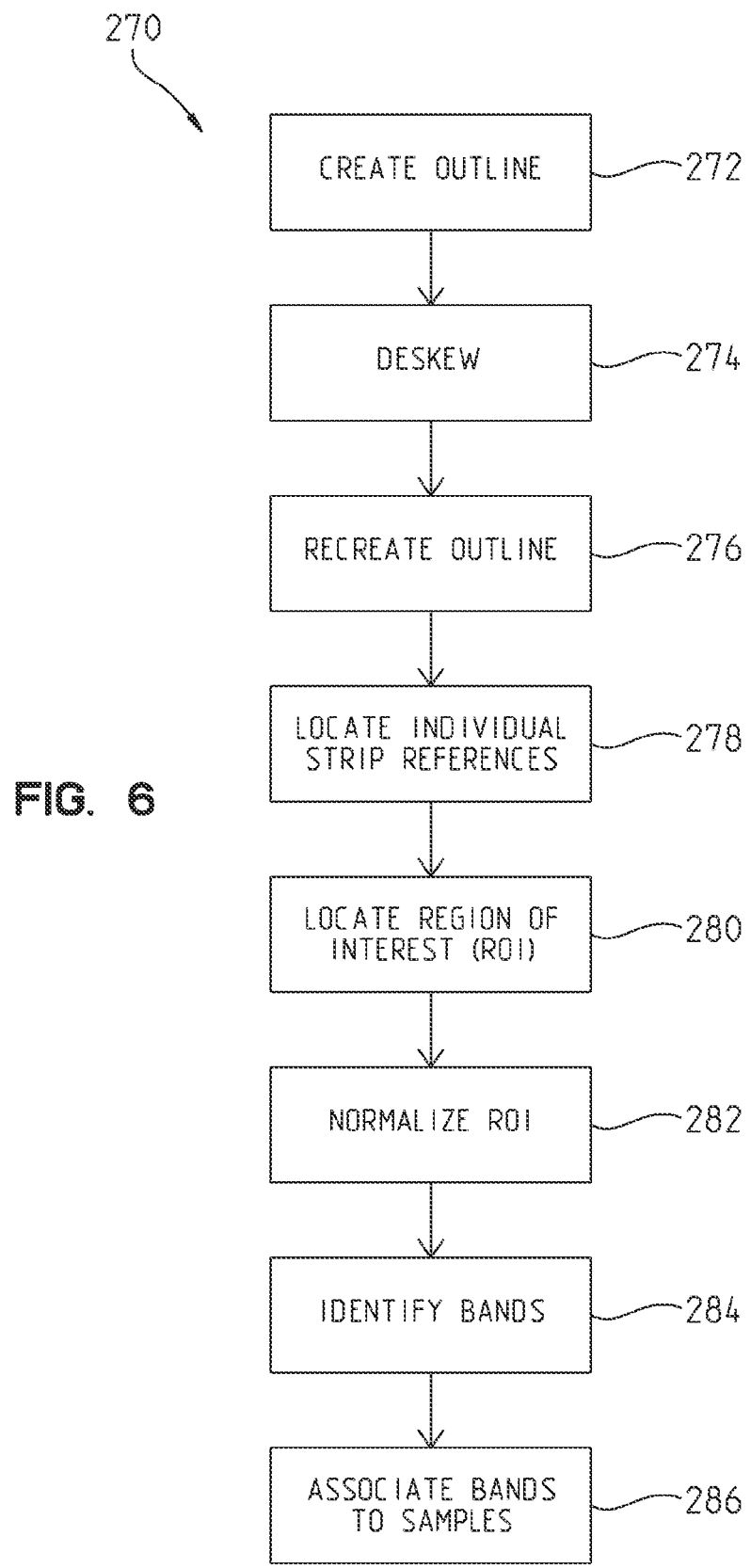
FIG. 6 illustrates an exemplary processing sequence of the system of FIG. 4.
Figure 7:
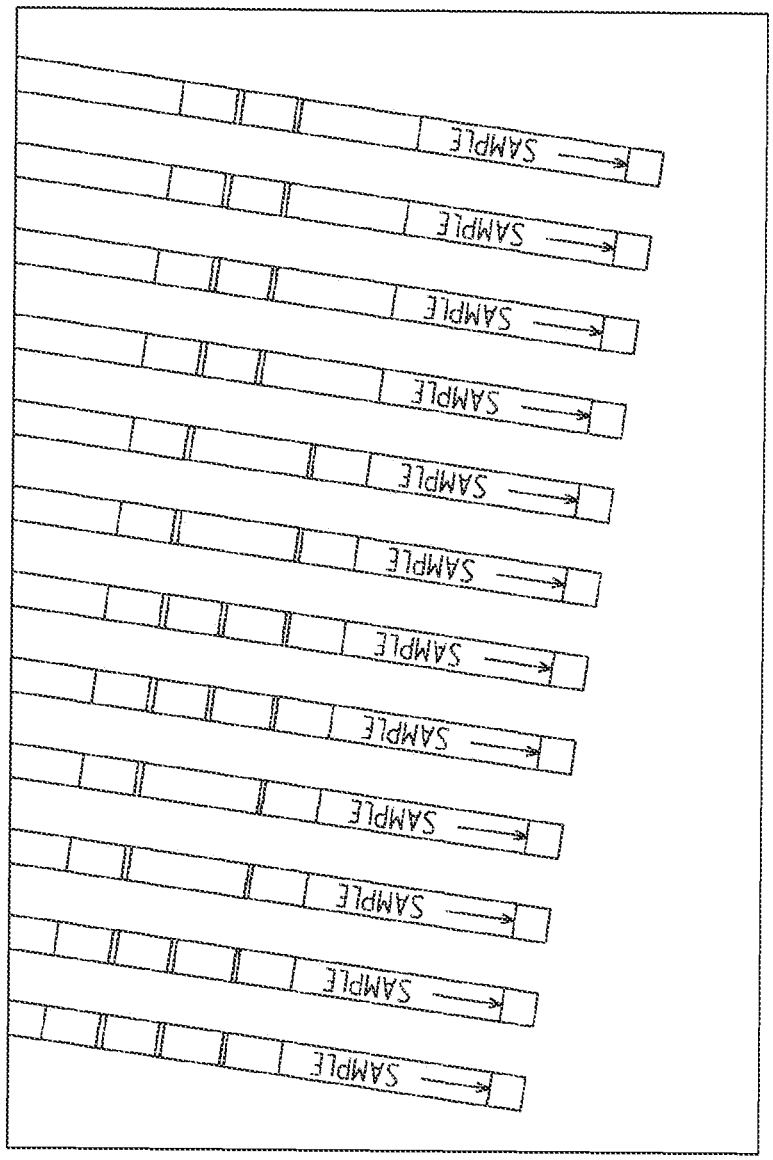
FIG. 7 illustrates an exemplary original image of an exemplary test strip comb member captured with the system of FIG. 4.

Referring to FIG. 6, an exemplary processing sequence 270 of controller 210 is shown. An outline of test strip comb member 120 is determined from image 124, as represented by block 272. An exemplary image 124 is shown in FIG. 7. This outline is used by image processing software 214 to determine an orientation of test strip comb member 120. In one embodiment, image processing software 214 alters the image to orient test strip comb member 120 such that fingers 122 are generally running vertically. In one embodiment, the outline extracted does not need to be a full outline, but rather only portions of the vertical edges of fingers 122 or other features of the comb member 122. The vertical edges between the fingers 122 may be identified based on a spacing between the edges which should correspond to one of a thickness of a finger or the spacing between adjacent fingers. In one embodiment, a left first vertical edge of a finger and a right vertical edge of a second finger are identified.

Figure 8:
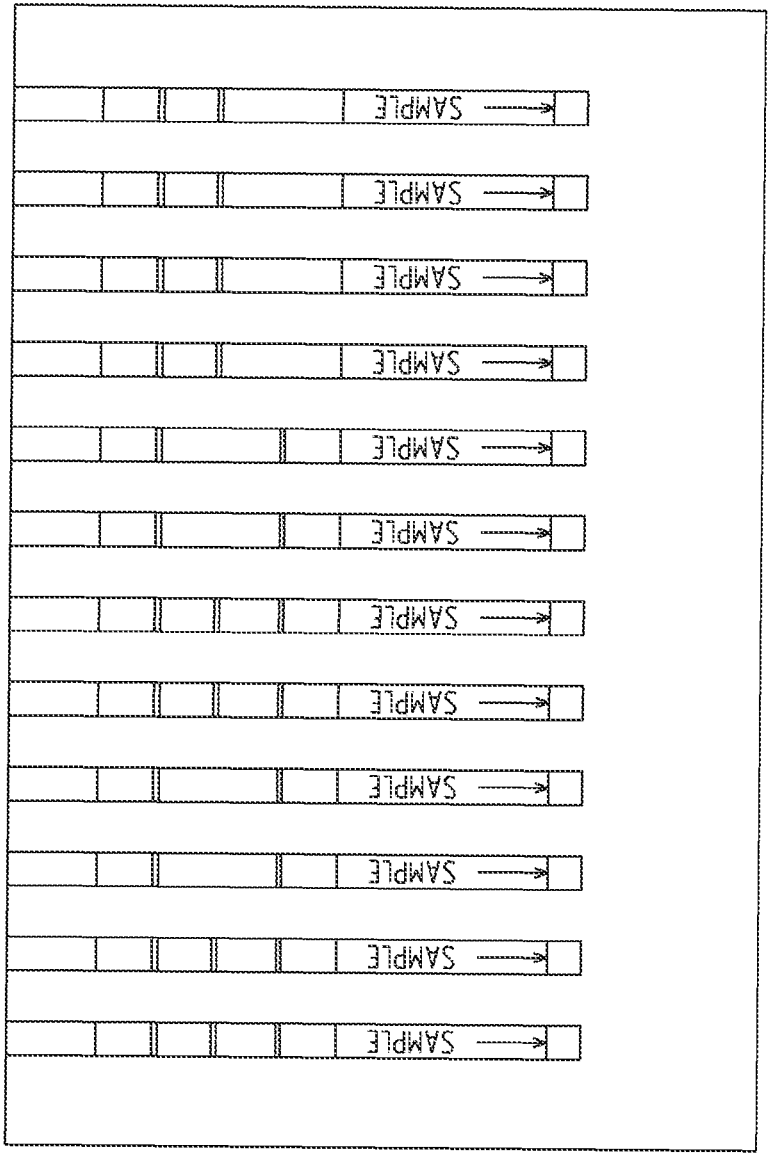
FIG. 8 illustrates a deskewed image of the exemplary test strip of FIG. 7.

If the image 124 of test strip comb member 120 is not oriented so fingers 122 run generally vertically, the image is deskewed by image processing software 214, as represented by block 274. An exemplary deskewed image is shown in FIG. 8. Once the image 124 is oriented correctly, the outline of test strip comb member 120 is once again determined, as represented by block 276. Once again, the outline does not need to be the entire outline of test strip comb member 120. This outline is used to determine references for each finger 122, as represented by block 278. In one embodiment, the reference for each finger is the lower edge of each of fingers 122. In one embodiment, a lower edge of each strip is determined by comparing a length of a horizontal outline feature to a known length of the finger 122. In this manner, debris in the image 124 may be discarded and inadvertently selected as a lower edge. Exemplary debris includes plant material, dirt, or other debris adhered to second plate 244.

Figure 9:
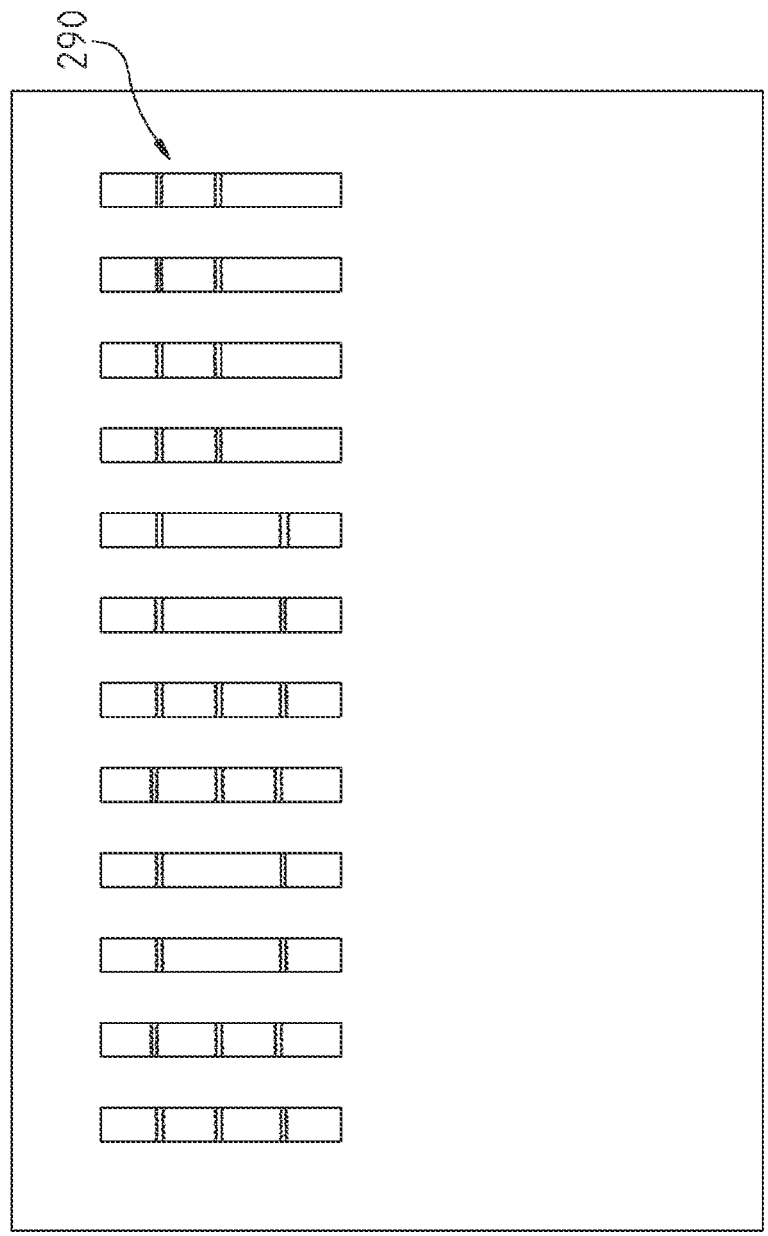
FIG. 9 illustrates the identification of regions of interest in the deskewed image of FIG. 8.
Figure 10:
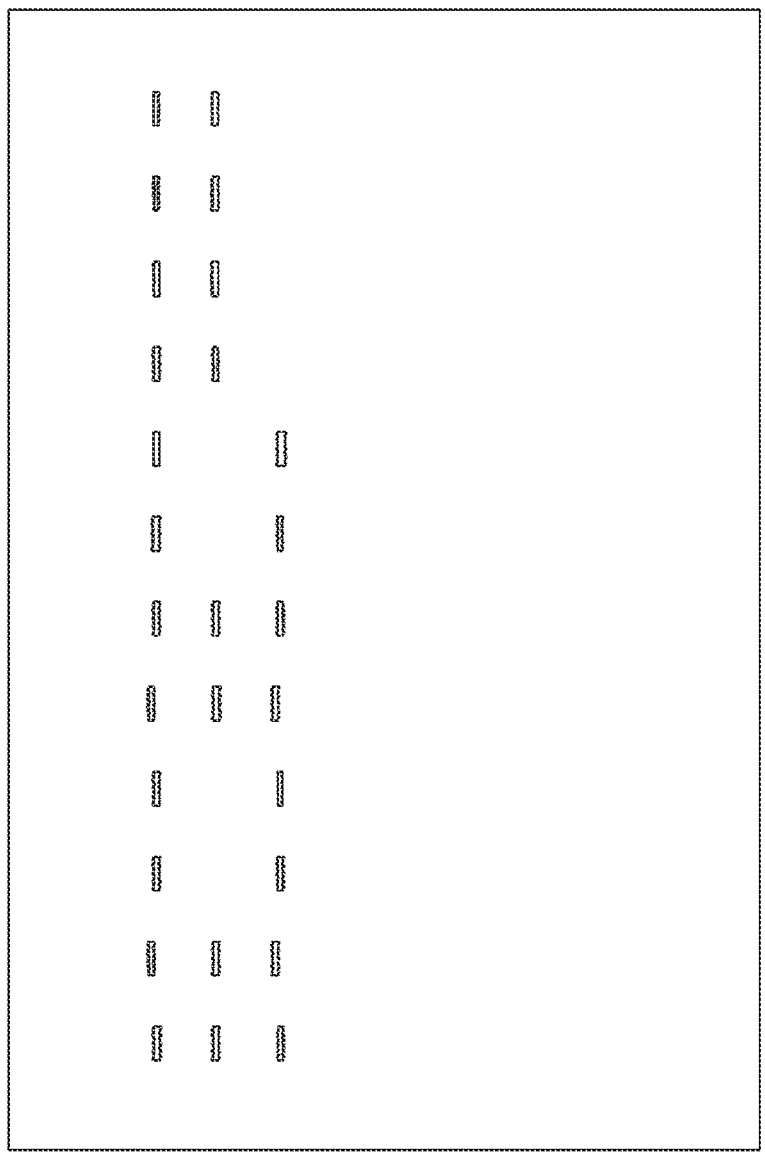
FIG. 10 illustrates the identification of bands within the regions of interest of FIG. 9.

Once the bottom of each finger 122 is known a region of interest 290 for each finger 122 is isolated from image 124, as represented by block 280. In one embodiment, the region of interest 290 for each finger corresponds to second region 126 of fingers 122. Referring to FIG. 9, an exemplary representation of the isolated regions of interest 290 for the deskewed image of FIG. 8 is shown. In one embodiment, the regions of interest 290 for each finger 122 is a set distance from the determined lower edge of the finger and the region of interest has a set length.

In one embodiment, the image of the regions of interest is normalized, as represented by block 282. In one embodiment, the normalization is a color equalization which removes color bias from the image. Exemplary bias may be green due to excess plant material in the image. Exemplary bias may be red due to dirt in the image.

As shown in FIG. 9, color bands are present in the regions of interest area of the various fingers 122. This image is used to identify the presence of bands in various areas of the regions of interest, as represented by block 284.

Figure 11:
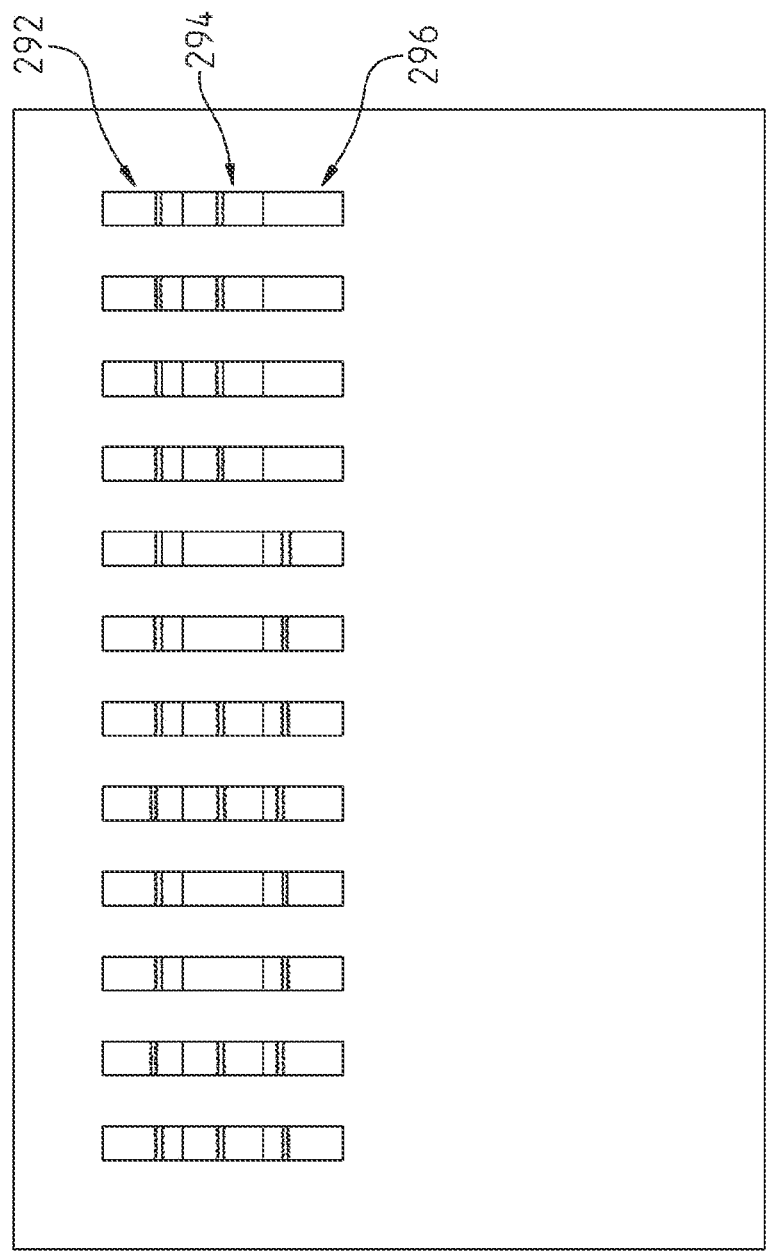
FIG. 11 illustrates the correlation of the identified bands in FIG. 10 to the content of the material in which the exemplary test strip comb member was inserted.

In one embodiment, based on the pixel color values each pixel is set to either first color or a second color. In one embodiment, the first color is white and the second color is black. Once the pixels have been colored one of the first color and the second color, the presence of a band in a defined region of a region of interest is determined. Referring to FIG. 11, each region of interest 290 includes three regions 292, 294, and 296. More or less regions may be included based on the configuration of test strip comb member 120. Since camera 202 is capturing the images of comb member 120 it may be possible to reduce the separation of the bands to achieve a resolution greater than standard human vision. Each of regions 292-296 correspond to the location of a potential band which indicates the presence or absence of a specific protein. As such, image processing software 214 examines the pixels in region 292 to determine the presence or absence of a first protein. Image processing software 214 examines the pixels in region 294 to determine the presence or absence of a second protein. Image processing software 214 examines the pixels in region 296 to determine the presence or absence of a third protein.

In one embodiment, image processing software 214 examines the pixels in a given region and compares the number of pixels in the region having a first color to a threshold. If the number exceeds the threshold then the protein is considered present. If the number does not exceed the threshold then the protein is considered absent. The following example illustrates this for a twelve finger comb which has two regions in the region of interest. As such, the comb is configured to detect the presence or absence of two proteins.

Returning to FIG. 6, image processing software 214 associates identified bands with the test tube that contained the finger 122, as represented by block 286.

EXAMPLE 2

In one embodiment, the test strip comb member 120 from seven test tube stands 100 were analyzed with system 200. Each test strip comb member 120 had 12 fingers and each test tube stand 100 held 96 test tubes. This equates to 672 samples. Each test tube stand 100 was analyzed in about 30 seconds. Of the 56 test strip comb members, 5 were incorrectly imaged by system 200. This equates to about a 9 percent error. Of the test strip comb members properly imaged, one finger 122 of one test strip comb member 120 was incorrectly read out of the 612 fingers read. This equates to an error of about 0.1 percent. The overall accuracy of system 200 was about 90.9 percent.

EXAMPLE 3

In one embodiment, the test strip comb member 120 from four test tube stands 100 were analyzed with system 200. Each test strip comb member 120 had 12 fingers and each test tube stand 100 held 96 test tubes. This equates to 384 samples. Each test tube stand 100 was analyzed in about 30 seconds. Of the 32 test strip comb members, 2 were incorrectly imaged by system 200. This equates to about a 6 percent error. Of the test strip comb members properly imaged, all fingers 122 were correctly read. The overall accuracy of system 200 was about 93.8 percent.

EXAMPLE 1

| Image A | | | | | | | | | | | | |
|---|---|---|---|---|---|---|---|---|---|---|---|---|
| | Finger | | | | | | | | | | | |
| | A | B | C | D | E | F | G | H | I | J | K | L |
| Number of white pixels listed | | | | | | | | | | | | |
| Control | 176 | 194 | 228 | 233 | 217 | 226 | 219 | 238 | 240 | 240 | 248 | 219 |
| Protein 1 | 150 | 143 | 0 | 0 | 160 | 164 | 0 | 0 | 180 | 193 | 205 | 175 |
| Protein 2 | 167 | 185 | 205 | 223 | 198 | 195 | 200 | 212 | 0 | 0 | 0 | 0 |
| Protein Present (based on 50 pixel threshold) | | | | | | | | | | | | |
| Control | Y | Y | Y | Y | Y | Y | Y | Y | Y | Y | Y | Y |
| Protein 1 | Y | Y | N | N | Y | Y | N | N | Y | Y | Y | Y |
| Protein 2 | Y | Y | Y | Y | Y | Y | Y | Y | N | N | N | N |

In the above example, the number of white pixels are listed for each of the two regions of the fingers of the twelve finger comb. These values are compared to the threshold value of 50 to associate the presence or absence of each of protein 1 and protein 2 with the substance in the corresponding test tube.

In one embodiment, a control region is provided on each finger. As shown in the above tables, in one embodiment, the control region should always provide a value above the threshold amount. The control region may be used as an error check on the analysis being performed.

In one embodiment, the pixels which are set to the first color are also examined to provide a measure of the level of protein expression. In one example, the average pixel color of the pixels which are to be set to the first color for a given region is determined. The average pixel color is used by the controller to classify the protein expression into one of at least two levels. In one example, up to eight levels of protein expression are provided. The level of protein expression is included in the protein marker information 220 in database 216.

In one embodiment, image processing software 214 includes a user interface which presents image 124 on a display device associated with controller 210. The user may review the image and select to redo the capture if the image is not suitable. One example of why the image may be unsuitable is that test strip comb member 120 was inserted into the slot between first plate 242 and second plate 244 backwards. The user interface includes an undo selection to perform this function.

In one embodiment, image processing software 214 includes a calibration routine whereby image processing software 214 may be calibrated to correctly recognize bands in the regions of interest 290 of an test strip comb member 120.

System 200 provides consistent analysis and is operator independent. The subjectivity between different operators is removed providing a consistent analysis. This consistent analysis is carried over from one batch of test strip comb members to another batch of test strip comb members. Pigment levels vary with different lots of test strip comb members purchased. The difference in pigment level may be avoided by "normalization" of images before decision making. The difference in pigment level may also be avoided by analyzing a standard with each lot. System 200 also archives the image 124 for further analysis if required; thereby enhancing record keeping. System 200 reduces processing time.

Figure 13:
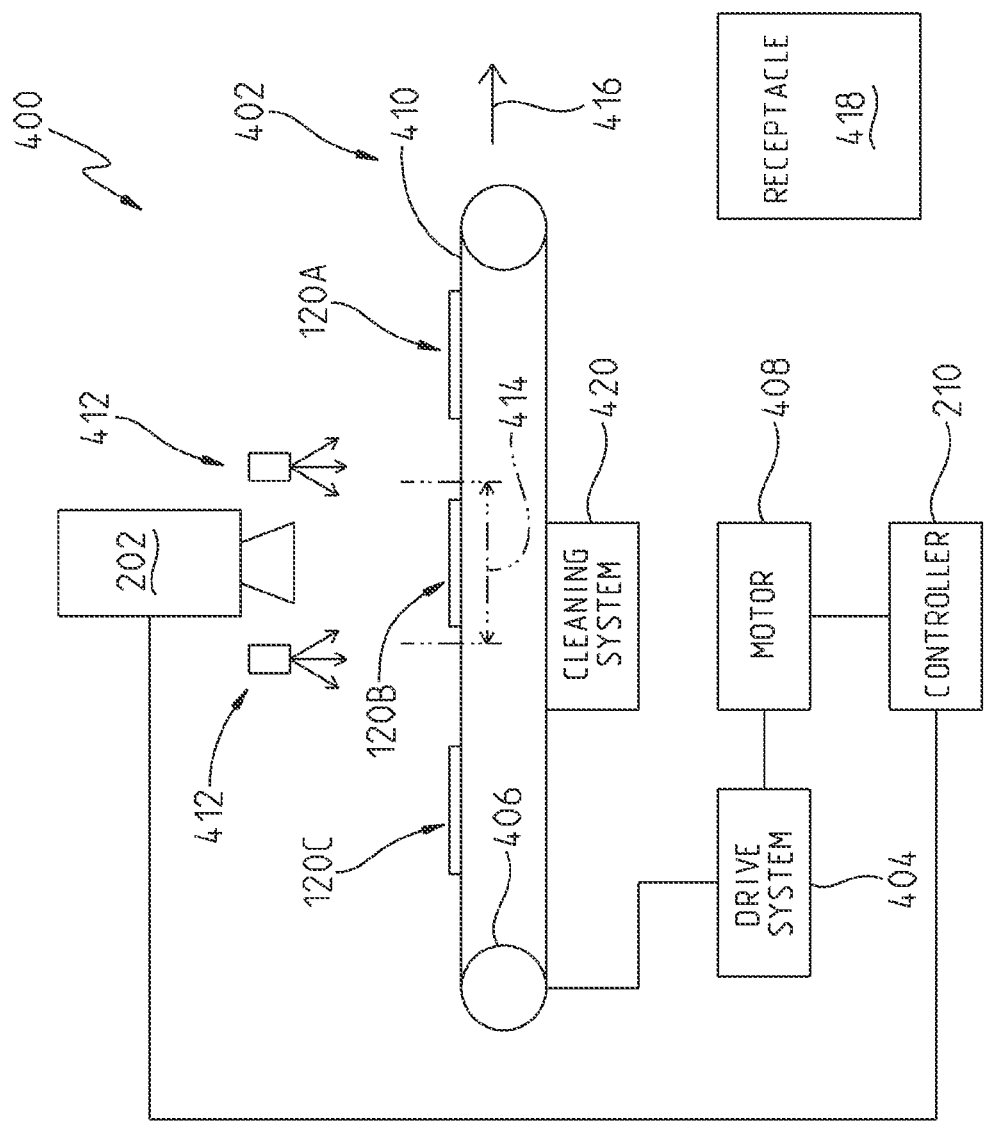
FIG. 13 illustrates a system for analyzing a plurality of comb members.

Referring to FIG. 13, system 400 is shown. System 400 processes images of comb members 120 generally in the same manner as system 200 or system 300. System 400 includes a conveyor system 402 which supports a plurality of test strip comb member 120. System 400 includes a drive system 404 which is coupled to a drive wheel 406 of conveyor system 402. Drive system 404 receives power from a motor 408 to drive wheel 406. In one embodiment, the operation of motor 408 is controlled by controller 210.

As shown in FIG. 13, camera 202 is positioned above a transport member 410 of conveyor system 402. Exemplary transport member 410 includes belts and other support surfaces. Additionally, one or more lights 412 are positioned above transport member 410 to illuminate a field of view region 414 of transport member 410 as viewed by camera 202. Lights 412 provide a generally uniform illumination of field of view region 414 of transport member 410. In one embodiment, the lights 412 may be directed away from transport member 410 for reflection off of a diffuse object, such as a screen, which redirects the light back towards field of view region 414 of transport member 410.

In the illustrated embodiment, drive system 404 causes transport member 410 to advance in direction 416 under the control of controller 210. In one embodiment, controller 210 does not control the operation of conveyor system 402, Rather conveyor system 402 is advanced at a constant rate not set by controller 210. The advancement of transport member 410 causes the individual test strip comb member 120 to be brought into field of view region 414 of transport member 410 to be imaged by camera 202. As illustrated, comb member 120A has exited field of view region 414 of transport member 410 and is ready to be moved to a receptacle 418, comb member 120B is currently in field of view region 414 of transport member 410 and is being imaged by camera 202, and comb member 120C is being advanced towards field of view region 414 of transport member 410 to be imaged by camera 202.

As mentioned herein, plant material and other debris may adhere to first plate 242. In system 400, transport member 410 is functioning as first plate 242. In one embodiment, transport member 410 has a generally dark color to provide contrast to test strip comb member 120. The upper surface of transport member 410, like first plate 242, may have plant material and other debris which adhere thereto. System 400 includes a cleaning system 420 which cleans the upper surface of transport member 410 to remove any undesired plant material or debris. The cleaning system 420 is positioned on the lower side of conveyor system 402. In one embodiment, cleaning system 420 includes a wiper which contacts the upper surface (now the lower surface) of transport member 410 to wipe away any plant material or debris.

Figure 14:
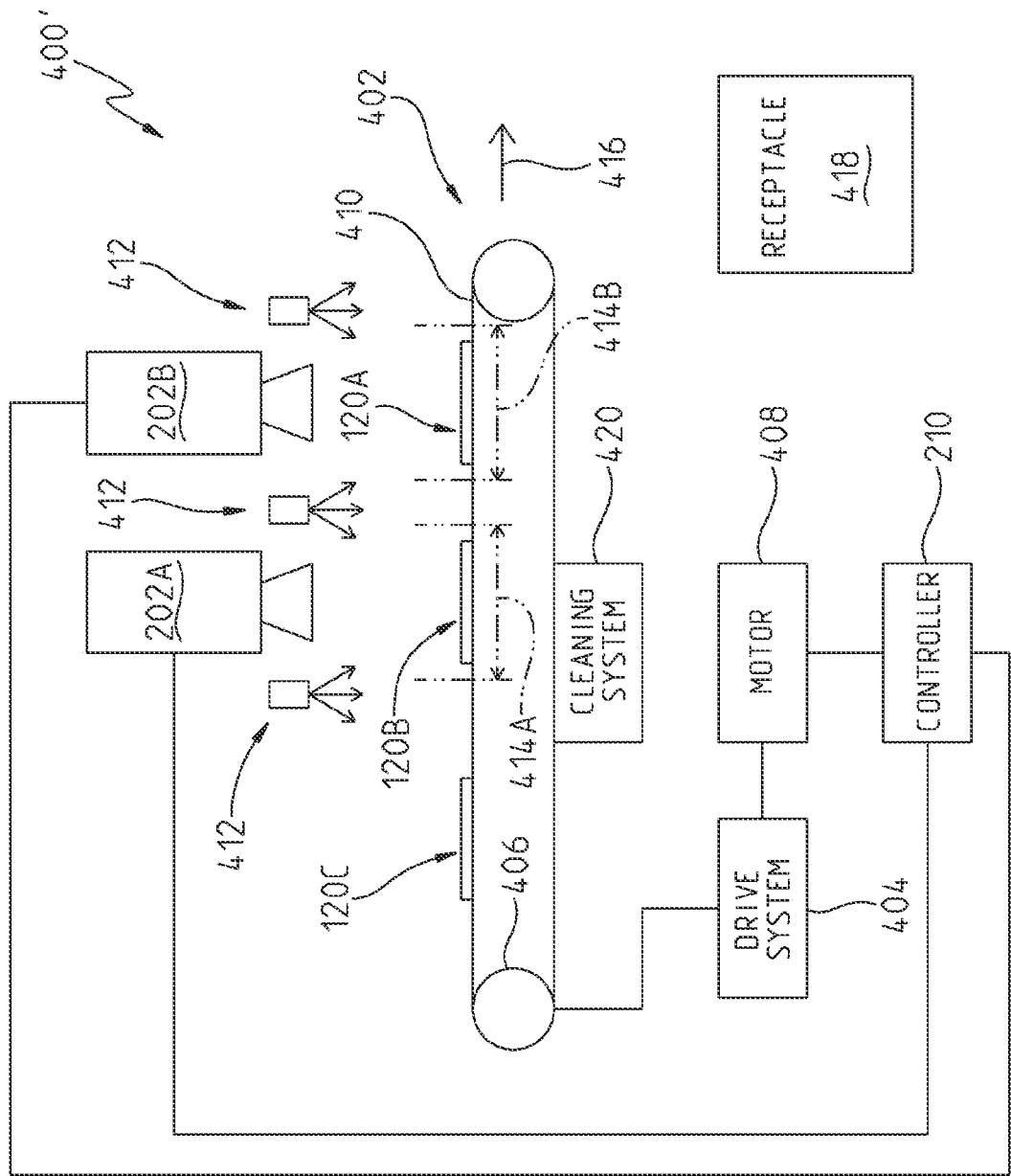
FIG. 14 illustrates the system of FIG. 13 including an additional camera system.

Referring to FIG. 14, a modified version of system 400' is shown. In system 400', a plurality of cameras, illustratively cameras 202A and 202B, are provided. Camera 202A images a first field of view region 414A of the upper surface of transport member 410 while camera 202B images a second field of view region 414B of the upper surface of transport member 410. Cameras 202A and 202B provide redundant images of each test strip comb member 120. As such, controller 210 may select a preferred image for further analysis for each of test strip comb member 120. Further, controller 210 may, for each test strip comb member 120, analyze both the image captured by camera 202A and the image captured by camera 202B. The results may then be compared for consistency of the identification of the presence or the absence of the proteins or other analyte.

Figure 15:
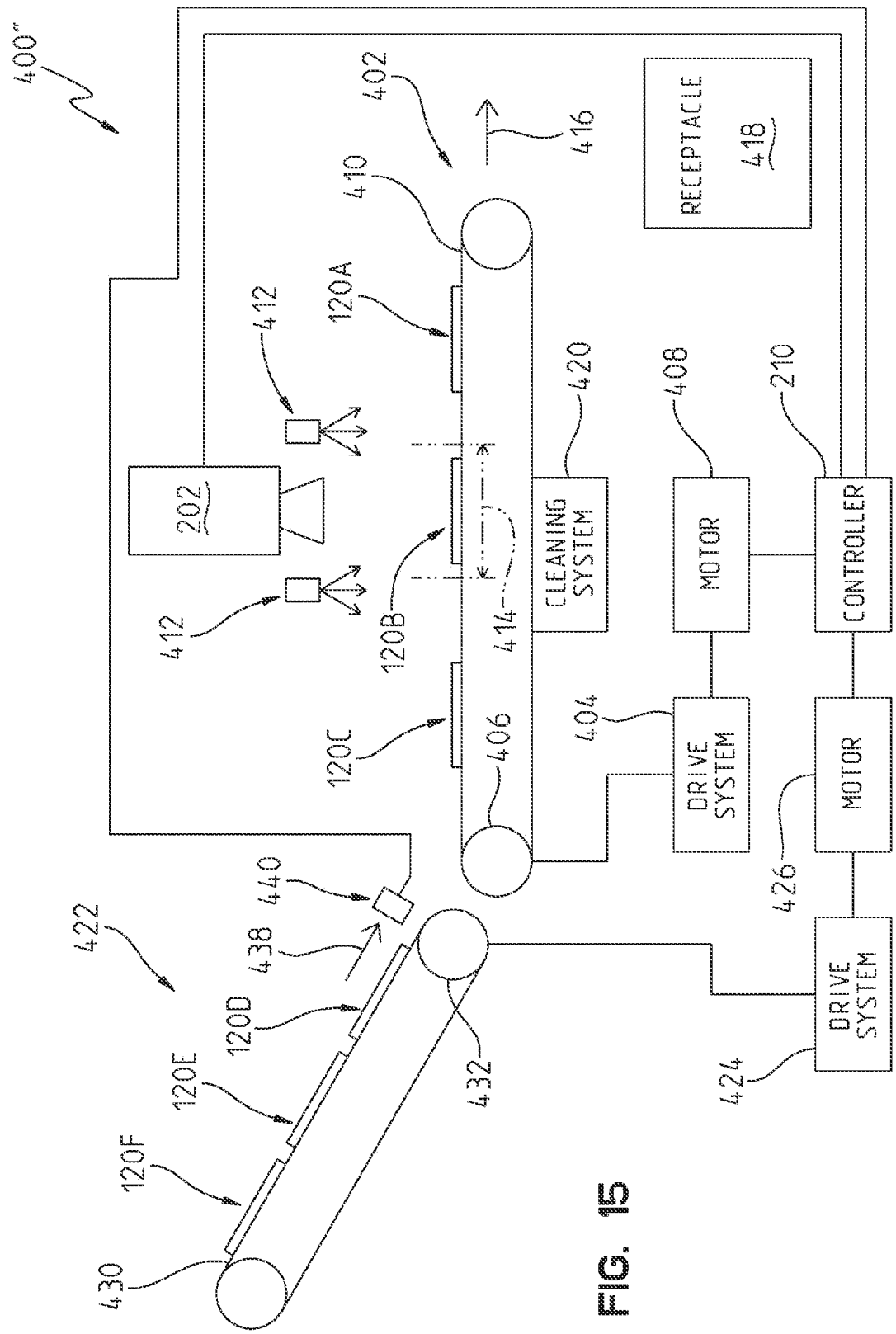
FIG. 15 illustrates the system of FIG. 13 including an input feeder system which controls the placement of comb members on the conveyor system.

In one embodiment, test strip comb member 120 are manually positioned on transport member 410 of conveyor system 402. In one embodiment, test strip comb member 120 are positioned on transport member 410 of conveyor system 402 by a feeder system. An exemplary feeder system 422 is shown in FIG. 15 as part of a modified system 400". In the illustrated embodiment, feeder system 422 is a second conveyor which carries test strip comb member 120 on a transport member 430 and operates to place the test strip comb member 120 on transport member 410 of conveyor system 402 for imaging by camera 202.

Transport member 430 is advanced in direction 438 by a drive system 424 which is driven by a motor 426. Motor 426 is controlled by controller 210. The spacing of test strip comb member 120 on transport member 430 may be random. However, feeder system 422 is controlled to place test strip comb member 120 onto transport member 410 with generally uniform spacing. As such, based on the placement of test strip comb member 120 on transport member 430, the speed of transport member 430 may need to be increased or decreased. In one embodiment, a sensor 440 is provided to indicate when a given test strip comb member 120 is located at an exit zone of feeder system 422. Exemplary sensors include optical sensors. Sensor 440 provides an indication of the presence or absence of a test strip comb member 120 in the exit zone of feeder system 422. Controller 210 in turn controls the advancement speed of transport member 430.

Although a second conveyor system is illustrated as feeder system 422, other types of feeder systems may be implemented. In one embodiment, feeder system 422 includes a tray to hold a plurality of comb members 120 and a pick-up mechanism to feed the comb members 120 one at a time onto conveyor system 402 similar to a printer feed tray. In one embodiment, system 400" further includes a second camera, similar to system 400'.

Figure 16:
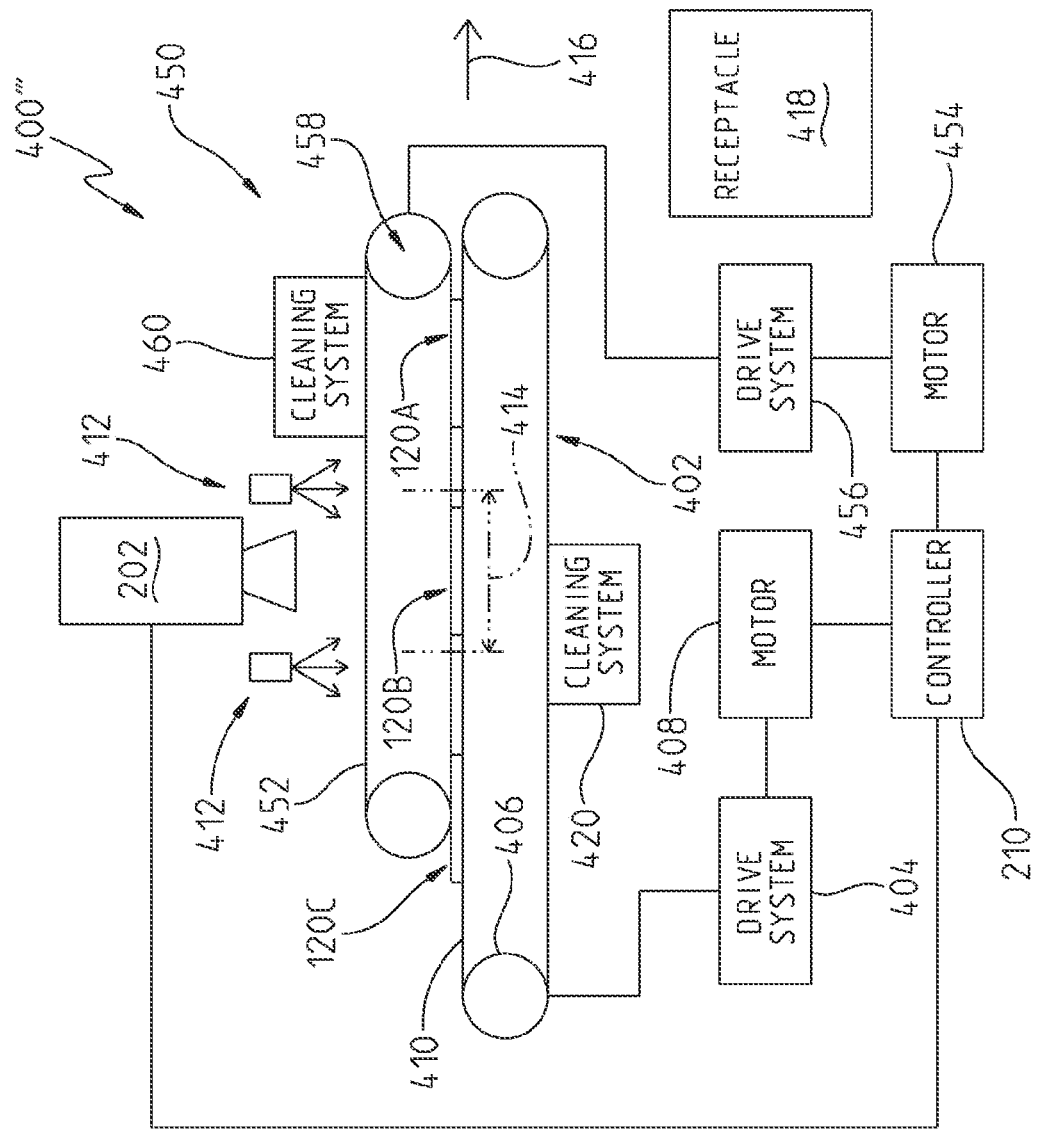
FIG. 16 illustrates the system of FIG. 13 including an additional conveyor system which controls a deformation level of the comb members.

Referring to FIG. 16, a modified system 400''' is shown. System 400''' includes a second conveyor system 450 which is positioned above conveyor system 402. A transport member 452 of second conveyor system 450 is at least partially transparent to permit camera 202 to continue to image a test strip comb member 120 positioned in field of view region 414. Second conveyor system 450 is driven by a drive system 456 which is powered by a motor 454. Motor 454 is controlled by controller 210. In one embodiment, controller 210 drives transport member 410 and transport member 452 at the same speed, but in opposite directions.

Second conveyor system 450 is positioned to generally flatten test strip comb member 120 as it is positioned within field of view region 414. Test strip comb member 120 may tend to curl when positioned on the upper surface of transport member 410. As such, a spacing of transport member 452 from transport member 410 may be selected to reduce any deformation of the fingers of test strip comb member 120. Transport member 452 is cleaned by a cleaning system 460 to remove any unwanted plant material or other debris. Cleaning system 460 may be a wiper unit.

In one embodiment, system 400''' includes a feeder system, similar to system 400", and/or a second camera, similar to system 400'.

Figure 17:
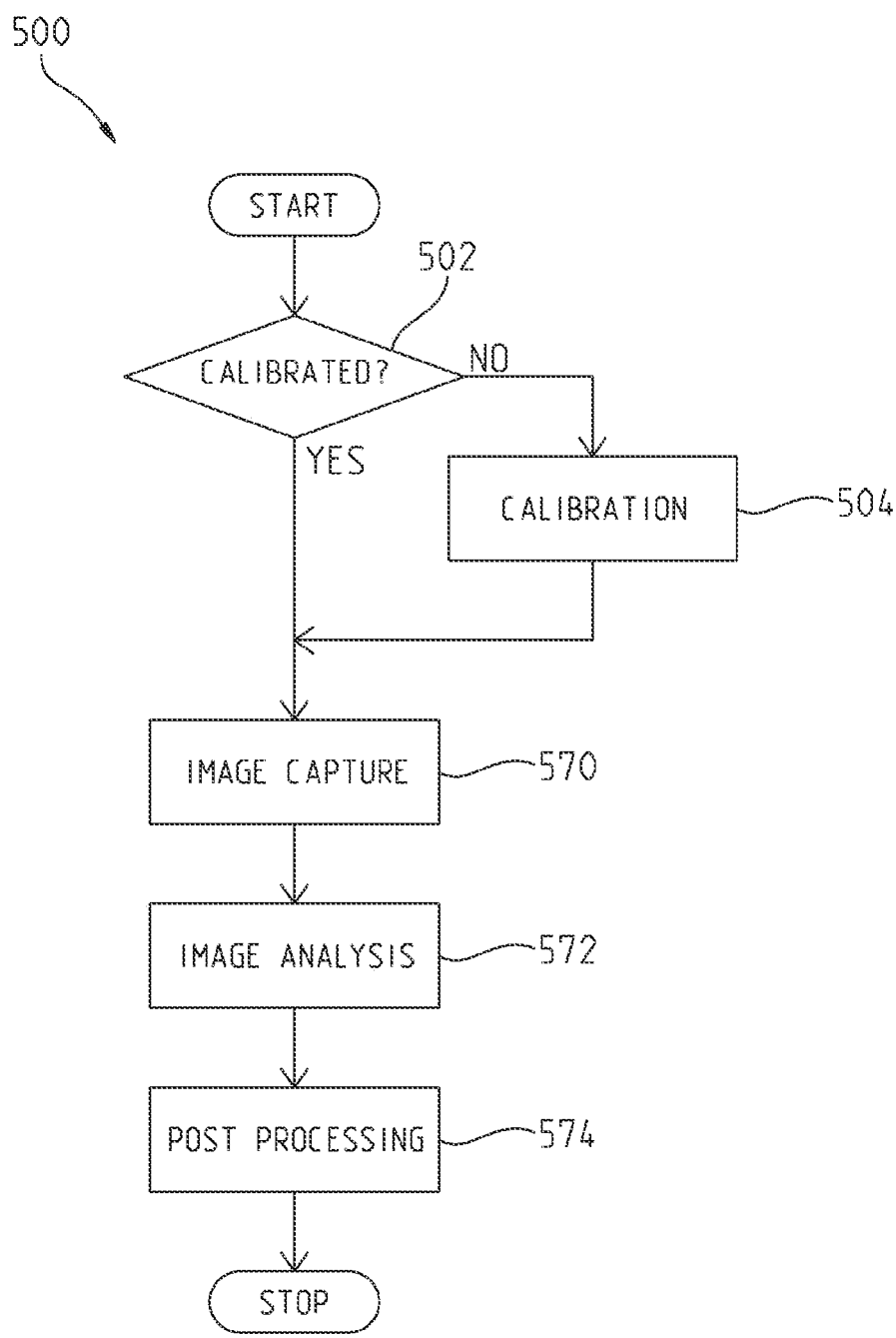
FIG. 17 illustrates an exemplary method of analyzing comb members.

Referring to FIG. 17, an exemplary process 500 for using any one of systems 200 and 400 is shown. The process will be described as being used with system 200 implementing reading device 300. One or more comb members 120 are received for processing. A decision is made whether the system 200 needs to has been calibrated or not, as represented by block 502. The output of light unit 320 may change over time resulting in a change in the color characteristics of the light and/or the intensity of the light. If a decision is made to calibrate the system 200, a calibration routine is carried out, as represented by block 504.

Figure 25:
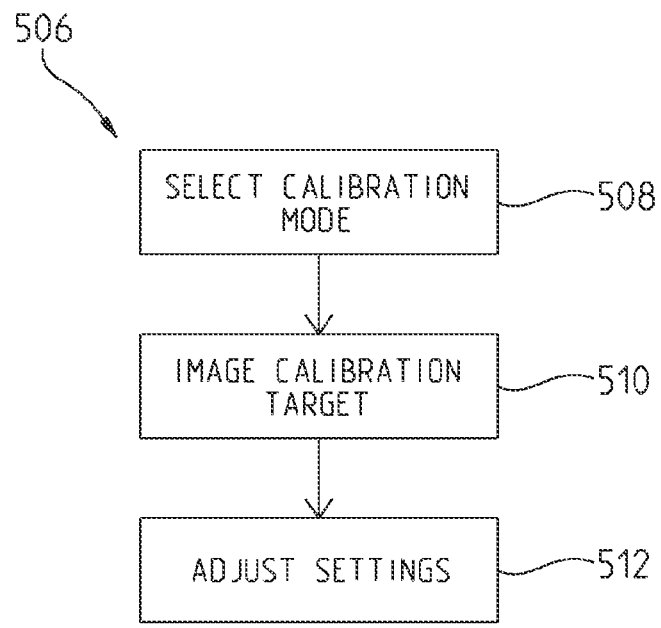
FIG. 25 illustrates an exemplary calibration processing sequence of FIG. 17.

An exemplary calibration routine 506 is shown in FIG. 25. Referring to FIG. 25, a user selects a calibration mode through a user interface of image processing software 214, as represented by block 508. An exemplary user interface 520 is shown in FIG. 27.

Figure 27:
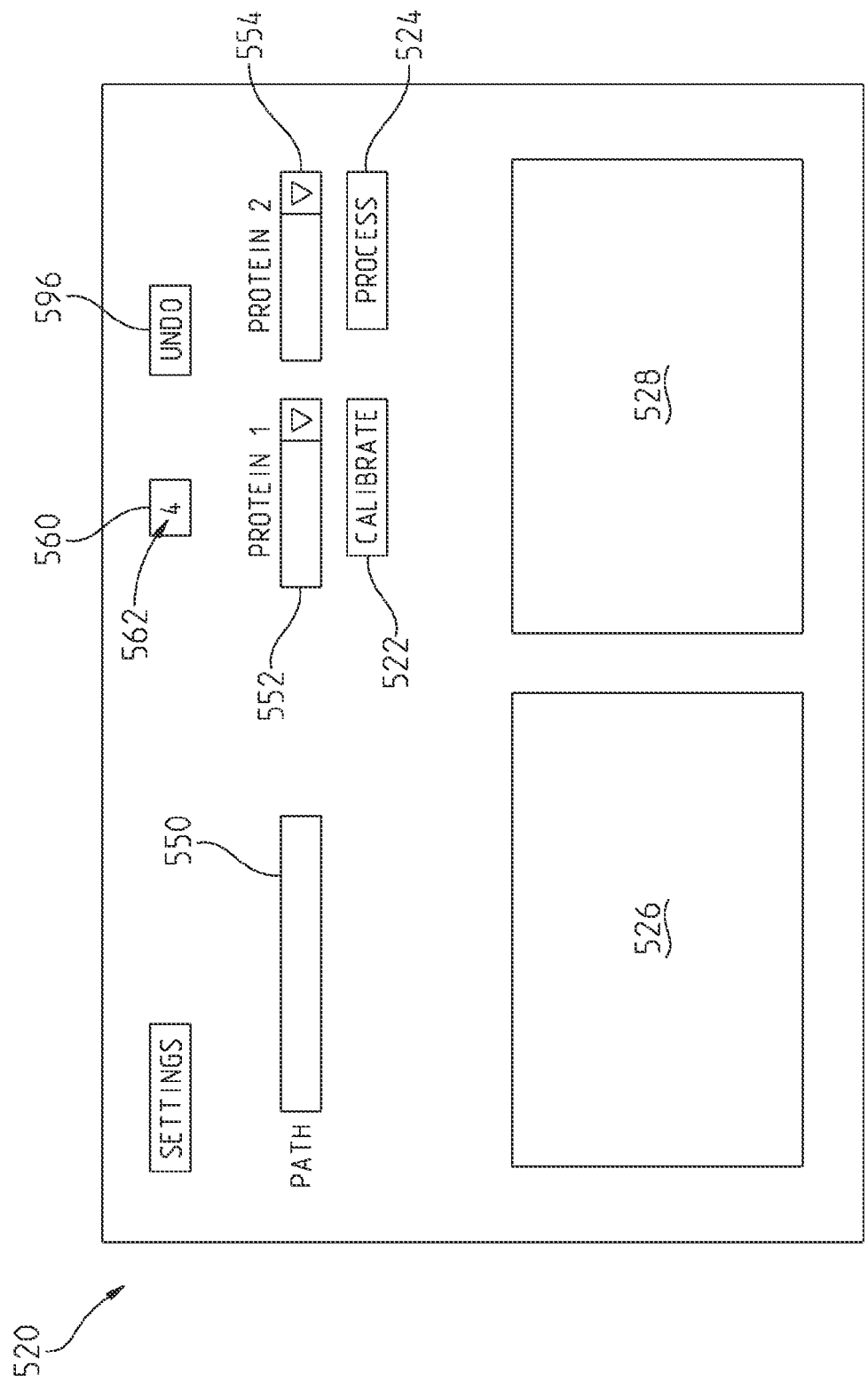
FIG. 27 illustrates an exemplary user interface.

Referring to FIG. 27, a calibrate input member 522 and a process input member 524 are provided as part of user interface 520. Each of input members 522 and 524 are shown as buttons which may be selected with a mouse or by depressing the corresponding area on a touch screen, however any suitable input member may be implemented. To enter calibration mode, an operator selects the calibrate input member 522. To enter a processing mode to capture images of comb members 120, an operator selects the process input member 524. A first portion 526 of user interface 520 provides the live image from camera 202. A second portion 528 of user interface 520 provides the most recent stored image selected for processing.

Returning to FIG. 25, a calibration target is imaged with camera 202, as represented by block 510. The calibration target provides a reference for image processing software 214 to determine one or more settings for analyzing images of comb members 120. These settings may be stored in a settings file 213 (see FIG. 4). In one embodiment, these settings may be user defined and are settable by selecting the settings input member 530 (see FIG. 27) of user interface 520. In one embodiment, these settings are set by image processing software 214. In one embodiment, an operator turns on light source 320 for at least ten minutes to allow light source 320 to reach a steady state condition.

Figure 26:
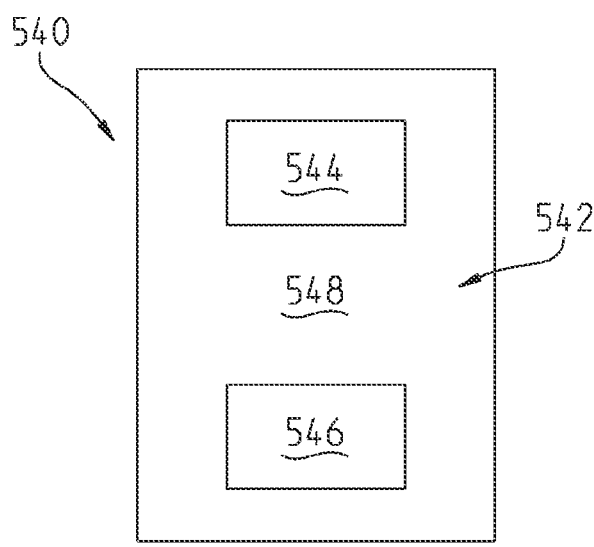
FIG. 26 illustrates an exemplary calibration target.

An exemplary calibration target 540 is shown in FIG. 26. Calibration target 540 generally includes a background 542 having a first color, a first region 544 having a second color, and a second region 546 having a third color. In one embodiment, the first color is white, the second color is red, and the third color is blue. During step 510, an image of calibration target 540 is captured. Image processing software 214 reviews the captured image and determines one or more settings associated with camera 202. In one example, based on the pixel values for a central region 548 of background 542 are analyzed to determine the current brightness of light source 320 and the pixel values of first region 544 and second region 546 are analyzed to determine the current color balance of light source 320.

Returning to FIG. 25, any changes to the settings from the calibration step are stored in settings file 213, as represented by block 512. Exemplary settings include exposure time, red balance, and blue balance.

Returning to FIG. 17, if a calibration mode is not selected a process mode is selected. In one embodiment, image processing software 214 defaults to the process mode. In one embodiment, the process mode is selected with the process input member 524. Prior to analyzing any test strip comb member 120, an operator specifies certain criteria to image processing software 214 through user interface 520.

Turning to FIG. 27, an operator specifies a file path with input 550. Further, an operator may specify a first protein that the comb members 120 are targeted for with a first protein input member 552 and a second protein that the comb members 120 are targeted for with a second protein input member 554. In the illustrated embodiment, first protein input member 552 and second protein input member 554 are drop-down lists which are populated with proteins stored in a protein database 215 (see FIG. 4).

Once all of the selections have been made by an operator, image processing software 214 indicates to the operator that it is ready to analyze test strip comb member 120 with an indicator 560. In one embodiment, indicator 560 is a colored region which has a first color, such as green, when image processing software 214 is ready to capture an image and a second color, such as red, when image processing software 214 is not ready to capture an image. In one example, indicator 560 further includes a numerical indicator 562 which indicates to the operator which comb member in a test tube stand 100 image processing software 214 has just read. Image processing software 214 has stored values which tell image processing software 214 how many combs are in a test tube stand 100, the number of fingers each test strip comb member 120 has, and information regarding the location of the regions of interest on the individual fingers. In one embodiment, these settings are stored in settings file 213 and are modifiable by the operator. In one embodiment, these settings are not stored in settings file 213 and are not accessible by the operator.

In one embodiment, indicator 560 is green when numerical indicator 562 is less than a total number of comb members 120 expected for a test tube stand 100 and red while an image is being processed or once the target number of test strip comb member 120 are analyzed for a given test tube stand 100. Prior to moving on to the next test tube stand 100 of test strip comb member 120, an operator may change the input for input 550 and potentially for one or both of first protein input member 552 and second protein input member 554.

Returning to FIG. 17, for each comb member 120, image processing software 214 stores an image, as represented by block 570. Image processing software 214 further analyzes the stored image, as represented by block 572. Image processing software 214 then performs post processing on the analyzed data, as represented by block 574. The post processing includes storage of the analyzed data and reporting. In one embodiment, once all of the comb members 120 for a test tube stand 100 have been analyzed, image processing software 214 outputs a result table indicating the presence or absence of each of protein 1 and protein 2 for each finger of each comb member 120. In one example, this information is output as a text file. In one embodiment, the results are stored in a database along with a link to the stored images. In one embodiment, a report is generated including the stored image and any results information.

Figure 18:
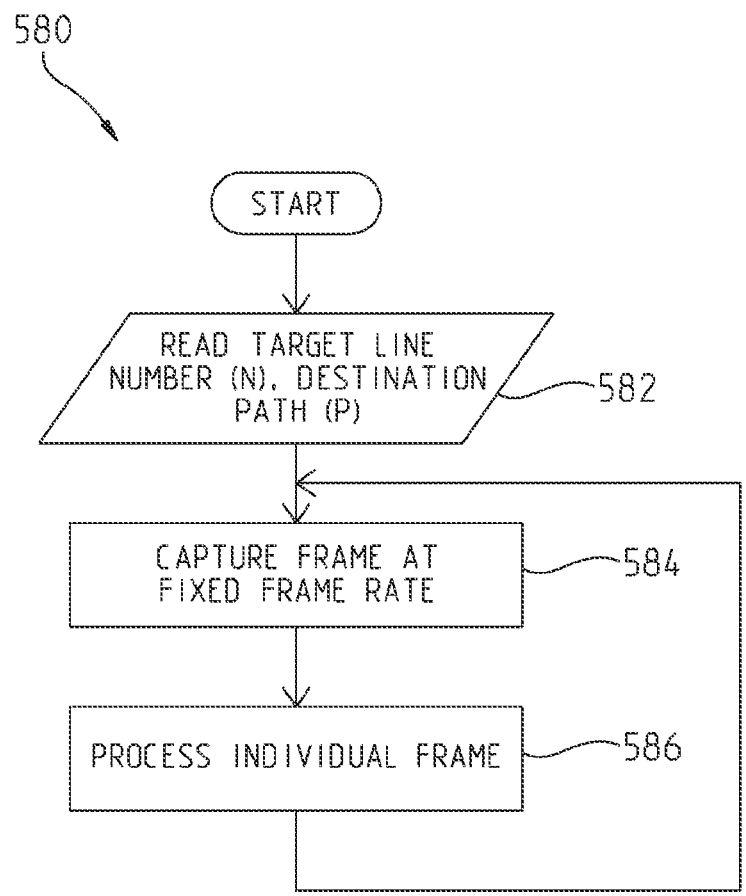
FIG. 18 illustrates an exemplary image capture processing sequence.

Referring to FIG. 18, an exemplary image captured processing sequence 580 of image processing software 214 is shown. Various parameters are read from settings file 213, as represented by block 582. In one embodiment, all settings stored in settings file 213 are read into image processing software 214 at the same time. Exemplary parameters read in from settings file 213 include the destination path (P) for images and the target line number (N). The target line number (N) corresponds to the sensor or trigger row for detecting when a test strip comb member 120 is present. In one embodiment, camera 202 has a 1280 by 960 resolution. The target line number (N) is selected to be low enough in the image that given the size of test strip comb member 120 all of the regions of interest of the fingers of test strip comb member 120 are visible in the image. As explained herein in connection with FIGS. 19A and 19B, when a condition is met for the target line number (N) the corresponding image is stored.

Returning to FIG. 18, image processing software 214 captures images at a fixed frame rate, as represented by block 584. In one embodiment, the fixed frame rate is twenty frames per second. Each captured frame is processed by an individual frame processing sequence to determine if it should be stored as the image of the current comb, as represented by block 586.

Figure 19A:
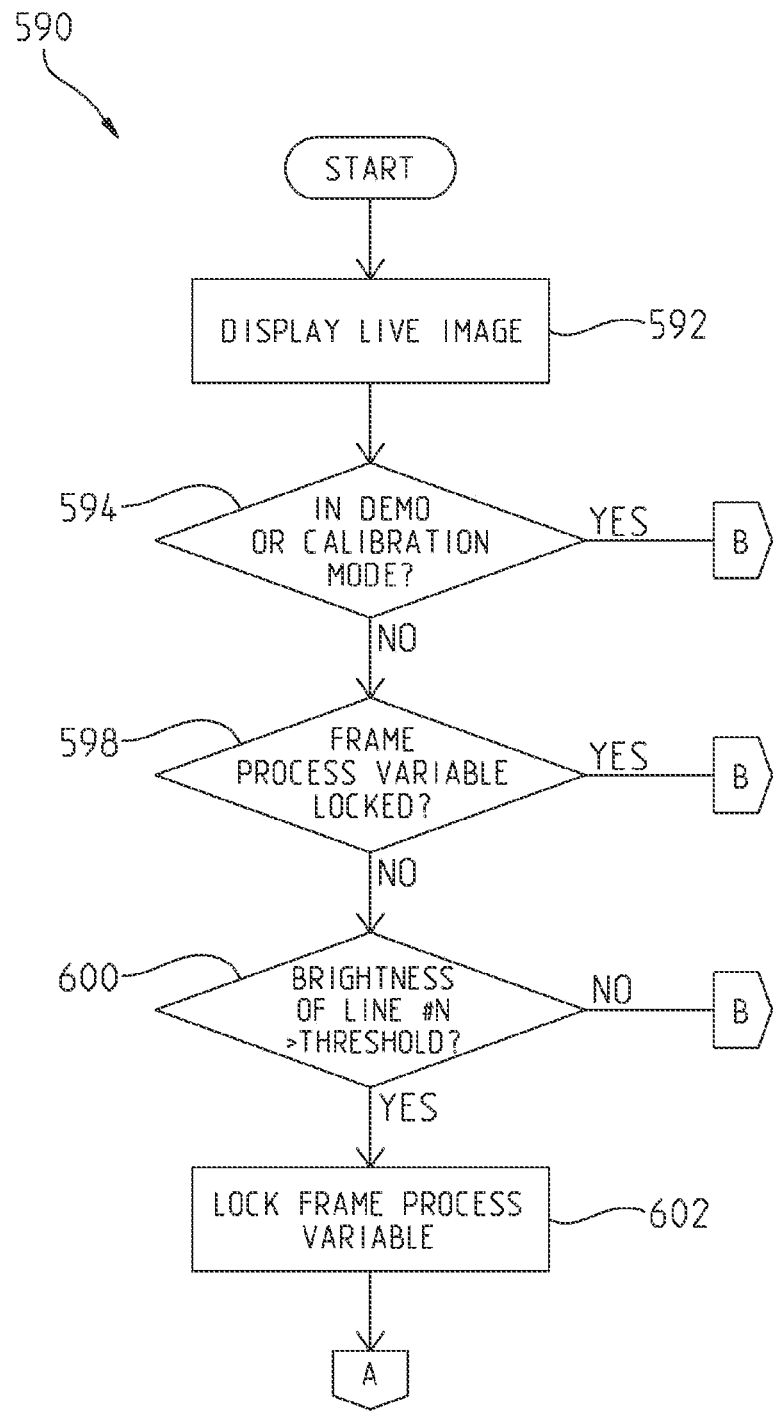
FIGS. 19A and 19B illustrate an exemplary image frame processing sequence.
Figure 19B:
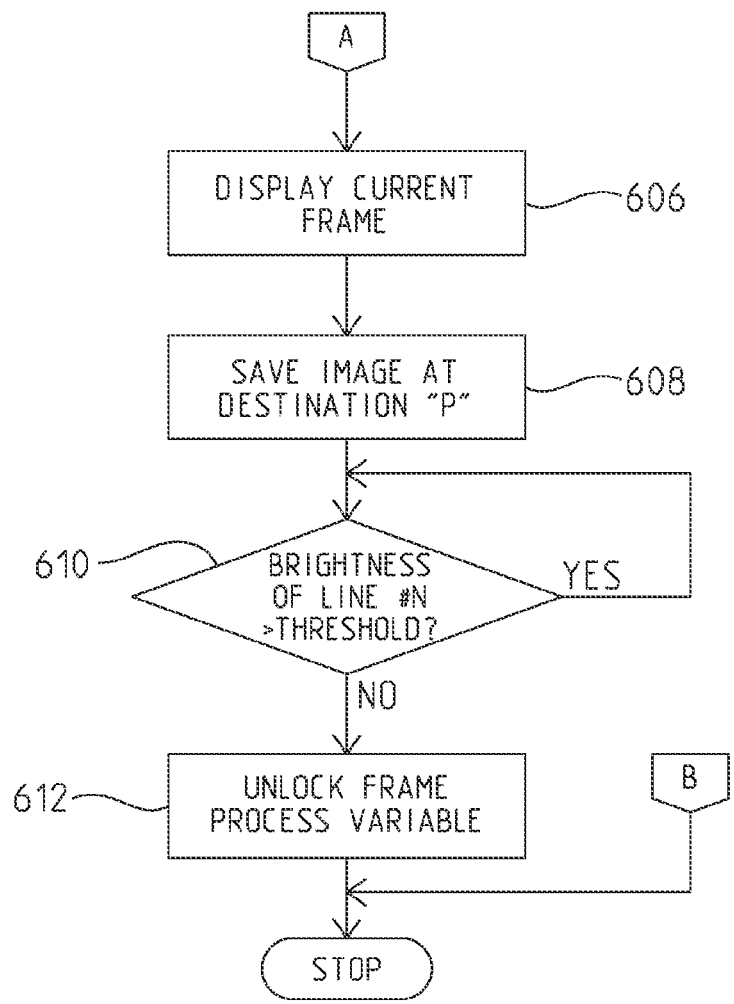

An exemplary individual frame processing sequence 590 of image processing software 214 is shown in FIGS. 19A and 19B. Referring to FIG. 19A, the current captured frame is displayed in first portion 526 of user interface 520, as represented by block 592. Image processing software 214 determines if it is in a calibration mode or a demo mode, as represented by block 594. If the image processing software 214 is in either a calibration or demo mode, the individual frame processing sequence is complete and image processing software 214 returns to block 584 in FIG. 18. If image processing software 214 is not in either a calibration or demo mode, image processing software 214 determines if a frame process variable is locked, as represented by block 598. When a frame is being stored, the frame process variable is set to LOCK. This indicates to image processing software 214 to not analyze any further images captured by camera 202 until the storing of the frame is complete. If the frame process variable is set to UNLOCK, meaning no image is currently being stored, image processing software 214 determines if the current captured frame includes an image of a test strip comb member 120, as represented by block 600.

In block 600, image processing software 214 analyzes the pixels of the target line number (N), such as row 600. Image processing software 214 first computes an average brightness for all of the pixels in the target row. Since camera 202 is a color camera, for each pixel an average brightness is the average brightness of the red value, the green value, and the blue value of that pixel. This average brightness for a given pixel is then averaged with all of the pixels of the target row to provide the overall average brightness for the target row. In one embodiment, each pixel has a brightness level in the range of 0 to 255. Image processing software 214 compares the average brightness value for the target row to a first threshold value. In one embodiment, the first threshold value is 150. If the average brightness value for the target row exceeds 150, then image processing software 214 continues to review the frame. If not, image processing software 214 returns to block 584.

If the average brightness value for the target row exceeds 150, then image processing software 214 determines the spread of the brightness value. If a comb is present many pixels in the target row should have a high brightness value. Image processing software 214 determines the number of individual pixels in the target row that exceed the first threshold. If this number exceeds a second threshold then image processing software 214 continues with individual frame processing sequence 590. If not, image processing software 214 returns to block 584. In one embodiment, the second threshold is 300 pixels.

If the frame has satisfied the second threshold, image processing software 214 sets the frame process variable to LOCK, as represented by block 602. Image processing software 214 then displays the frame in second portion 528 of user interface 520, as represented by block 606, and stores the frame, as represented by block 608. The display of the frame in second portion 528 of user interface 520 indicates to the operator that this frame is being stored for the current test strip comb member 120. If the frame looks satisfactory, the operator needs to do nothing further. The operator may present the next test strip comb member 120 once image processing software 214 exits individual frame processing sequence 590. If the frame does not look satisfactory, the operator may select an undo input 596 (see FIG. 27) of user interface 520. This alerts image processing software 214 that the next test strip comb member 120 detected needs to overwrite the last saved test strip comb member 120.

Once image processing software 214 finishes saving the frame, image processing software 214 checks to see if the target row of the next captured frame satisfies the thresholds described in connection with block 600. If yes, image processing software 214 continues to loop and check subsequent frame. If no, image processing software 214 sets the frame process variable to UNLOCK, as represented by block 612. When image processing software 214 sets the frame process variable set to UNLOCK, the numerical indicator 562 of indicator 560 is incremented as well and indicator 560 turns to green if further combs are to be analyzed.

Figure 20:
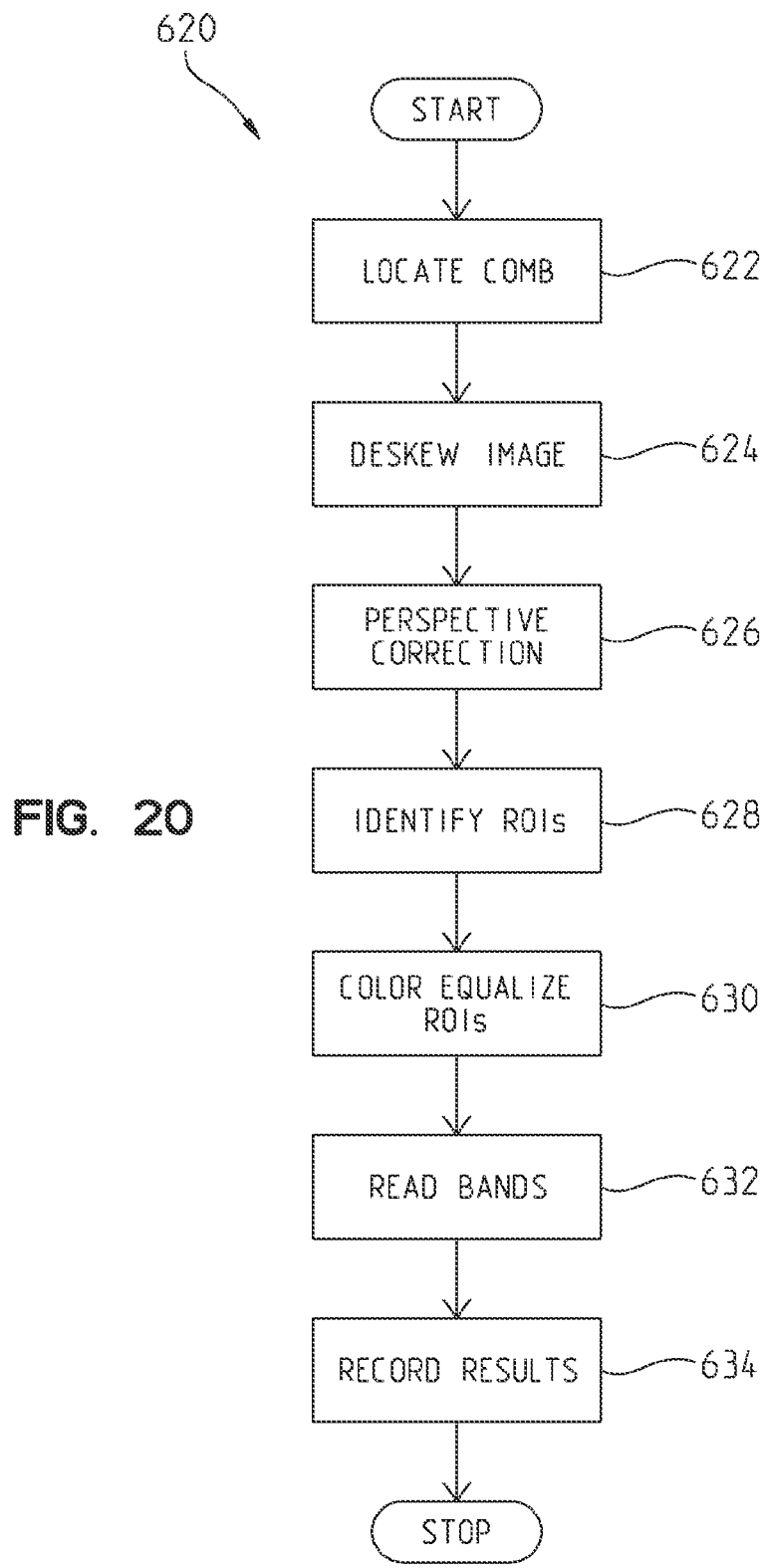
FIG. 20 illustrates an exemplary image analysis processing sequence.

Referring to FIG. 20, an exemplary image analysis processing sequence 620 is shown. Image analysis processing sequence 620 locates test strip comb member 120 in the stored image, as represented by block 622. Image analysis processing sequence 620 orients the stored image so that test strip comb member 120 is shown in a preferred orientation, as represented by block 624. In one embodiment, the preferred orientation has the fingers running generally vertical. Image analysis processing sequence 620 further corrects the stored image for any perspective distortion, as represented by block 626.

Image analysis processing sequence 620 identifies one or more regions of interest associated with test strip comb member 120, as represented by block 628. In one embodiment, the region of interest for each finger corresponds to second region 126 of fingers 122 (see FIG. 3). In one embodiment, the regions of interest 290 for each finger is a set distance from the determined lower edge of the finger and the region of interest has a set length.

Image analysis processing sequence 620 color equalizes the regions of interest, as represented by block 630. By color equalizing the regions of interest, the background color may be taken into account. Often times the fingers may look green due to plant tissue which has discolored the finger 122 or reddish due to mud which has discolored the finger 122. In one embodiment, the region of interest for each finger is color-equalized independently of the other fingers. In one example, the average values for a region of interest including the bands are red=100; green=100; and blue=125. Each of the red, green, and blue components are scaled to result in the average values being red=150; green=150; and blue=150. This eliminates the effect of any overall color variation from one region to another region while maintaining the color variations within a given region.

Image analysis processing sequence 620 reads the bands in the regions of interest in each finger to determine if the target protein is present or absent, as represented by block 632. In one embodiment, each pixel in the band region is reviewed to see if it is indicative of the protein being present or absent. In one embodiment, if the red value of a pixel exceeds a red threshold, a blue value of a pixel is below a blue threshold, and a green value of a pixel is below a green threshold, then the pixel is indicative of the protein being present. Otherwise, the pixel is indicative of the protein being absent. By categorizing each pixel based on its individual red, blue, and green values instead of an overall average pixel value, image processing software 214 is able to take into account matrix effects. An exemplary matrix effect is when chlorophyll or some other plant material (other than the target protein) also binds at the band site on a finger. This may produce a distinctive band, but green in color instead of red. This distinction is picked up by looking at the component colors of a pixel instead of an overall average value of the pixel.

Image analysis processing sequence 620 also records the results for each protein (band) of each finger, as represented by block 634. In one embodiment, a qualitative measure (Y or N) is provided. The protein is considered to be present (Y) if a threshold number of pixels in the band met the component color criteria discussed above or absent (N) otherwise. In one embodiment, the threshold number is sixty pixels. In one embodiment, a quantitative measure is provided. An exemplary quantitative measure is the number of pixels in the band that met the component color criteria discussed above. This quantitative result may be used to provide a level of expression. The results are then stored either in a test strip database 216 or a text file.

Figure 21:
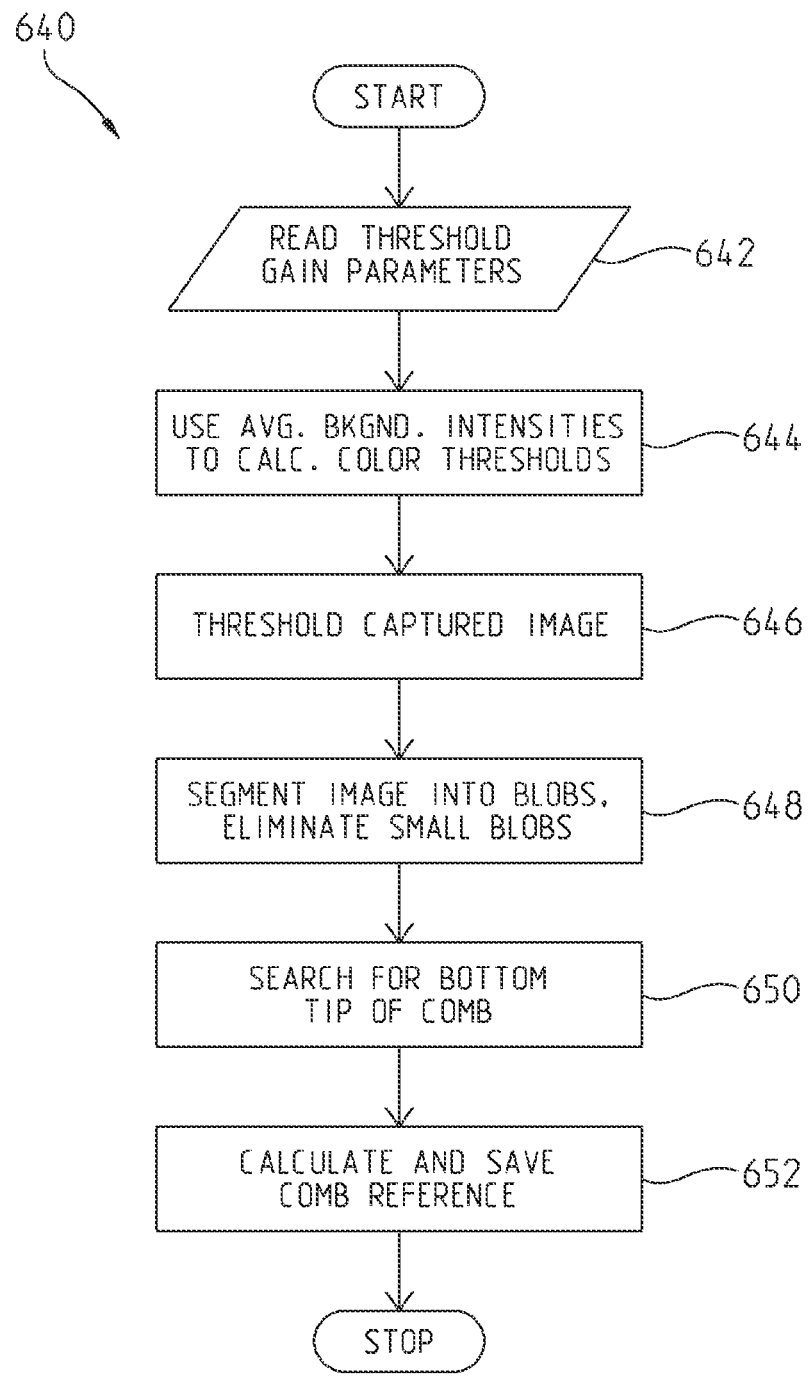
FIG. 21 illustrates an exemplary locate comb processing sequence of FIG. 20.

As mentioned in connection with block 622 of FIG. 20, image analysis processing sequence 620 locates the comb in the stored image. An exemplary processing sequence 640 for locating the comb 120 in the stored image is provided in FIG. 21. The image processing software 214 reads the threshold gain parameters and any other parameters from settings file 213, as represented by block 642. The parameters include a threshold value for number of contiguous pixels that qualify as a band versus a speck. The values from settings file 213 are read from settings file 213 at the beginning of the operation of block 572.

Processing sequence 640 uses average background intensities for the red values, blue values, and green values to determine color thresholds, as represented by block 644. This adjusts for the brightness of the light 320. As stated herein, a row (N) of the image is used as the trigger for determining when to store the image. The average background intensities are computed from a region of the stored image lower than row (N). The region is selected to not include any portions of the comb 120. An average background intensity value is found for each of red, green, and blue.

The stored image is then thresholded based on the average background intensities, as represented by block 646. The threshold is color-by-color to ensure that the regions that are dark blue or dark red are considered to be part of the comb 120. If the value for a pixel is greater than the threshold then the pixel is assigned a white value. Otherwise the pixel is assigned black.

The threshold image is then segmented to eliminate small blobs, as represented by block 648. Blobs may be caused by plant material on the comb 120 or otherwise in the field of view of camera 202. In one embodiment, the threshold image is scanned for a white pixel. This pixel is marked. Then all adjacent white pixels are marked and then all adjacent white pixels to those pixels are marked. This continues until no further adjacent white pixels are encountered. At that point, the number of pixels making up this connected region is compared to a threshold number. If greater than the threshold number the pixels remain white. Otherwise they are turned black. In one example, the threshold is 10 connected pixels. This continues until the whole image has been reviewed.

The location of the bottom of the test strip comb member 120 in the stored image is determined, as represented by block 650. In one embodiment, a row is selected in the middle of the image. Starting at the left side, the pixels in the row are examined until a white pixel is identified. Once a white pixel is identified, image processing software 214 moves down a row and determines if that pixel is a white pixel. If yes, image processing software 214 moves down another row. If no, image processing software 214 continues to the right until the next white pixel is reached. This stair-stepping continues until the right side of the stored image is reached. The row continuing the last identified white pixel is assigned as the bottom of the comb 120.

A comb reference is determined, as represented by block 652. The comb reference corresponds to a row in the stored image wherein the comb 120 is known to exist. In one embodiment, the comb reference is an offset up from the row identified as the bottom of the comb 120.

Figure 22:
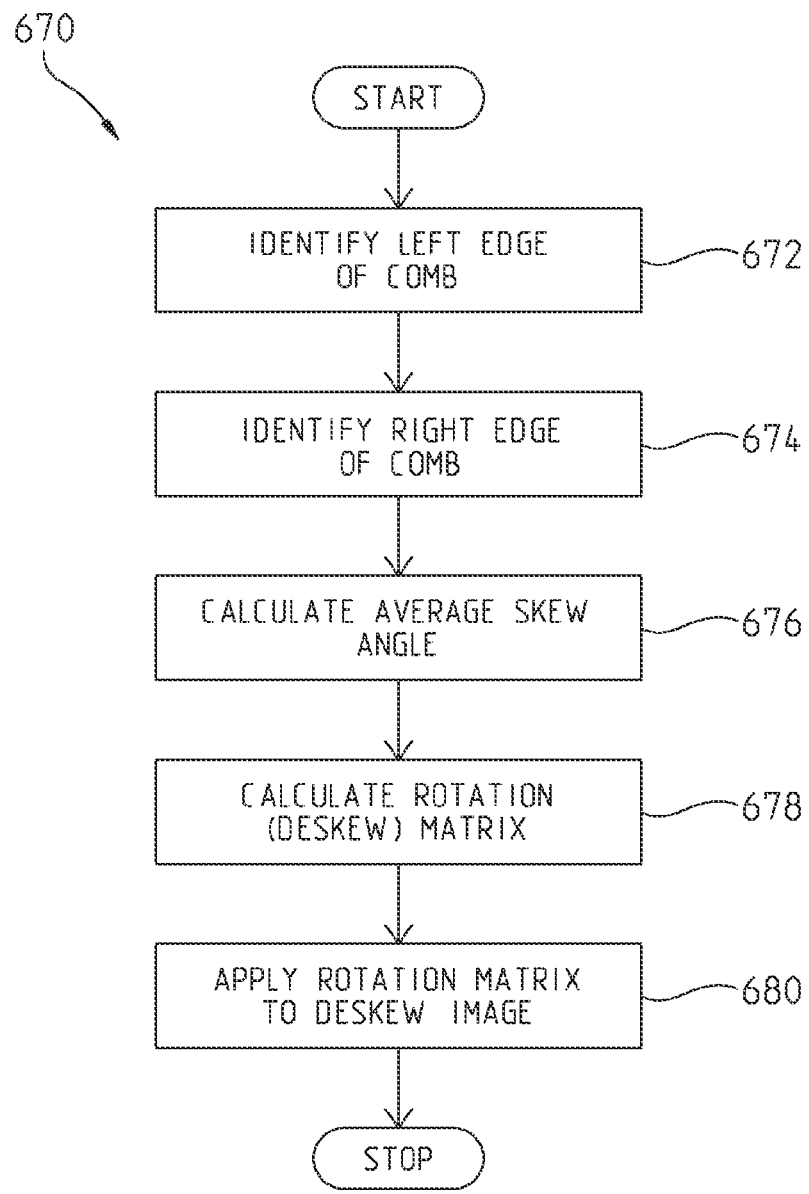
FIG. 22 illustrates an exemplary deskew image processing sequence of FIG. 20.

As mentioned in connection with block 624 of FIG. 20, image analysis processing sequence 620 deskews the comb in the stored image. An exemplary processing sequence 670 for deskewing the comb 120 in the stored image is provided in FIG. 22.

Image processing software 214 identifies a left edge 672 (see FIG. 3) of test strip comb member 120 and a right edge 674 (see FIG. 3) of test strip comb member 120, as represented by blocks 672 and 674. These edges are used to determine a skew angle for test strip comb member 120, as represented by block 676. Although, a left edge 672 and a right edge 674 are used, other features of the stored image may be used to determine a skew angle or rotation matrix of test strip comb member 120.

In one embodiment, the left edge is determined using a two-point determination for a line. At the left most pixel of the comb reference row, image processing software 214 moves to the right until a white pixel is encountered. This is marked as a first point. Next, image processing software 214 does the same at a row offset from the comb reference row, such as 100 rows lower. This pixel is marked as a second point. These two points are used to determine a line whose angle from vertical is a first skew angle. The right edge is determined in the same manner, but starting from the right most pixel and moving to the left. The resultant angle from vertical is a second skew angle. The average of these two skew angles is determined to be the skew angle for test strip comb member 120.

A deskew matrix is determined for the stored image, as represented by block 678. An exemplary rotation matrix is provided below wherein $\phi$ is the skew angle.

$$\begin{bmatrix} x_{new} \\ y_{new} \end{bmatrix} = \begin{bmatrix} \cos(\phi) & \sin(\phi) \\ -\sin(\phi) & \cos(\phi) \end{bmatrix} \begin{bmatrix} x_{old} \\ y_{old} \end{bmatrix}$$

The rotation matrix is then applied to the stored image to deskew the test strip comb member 120, as represented by block 680.

Figure 23:
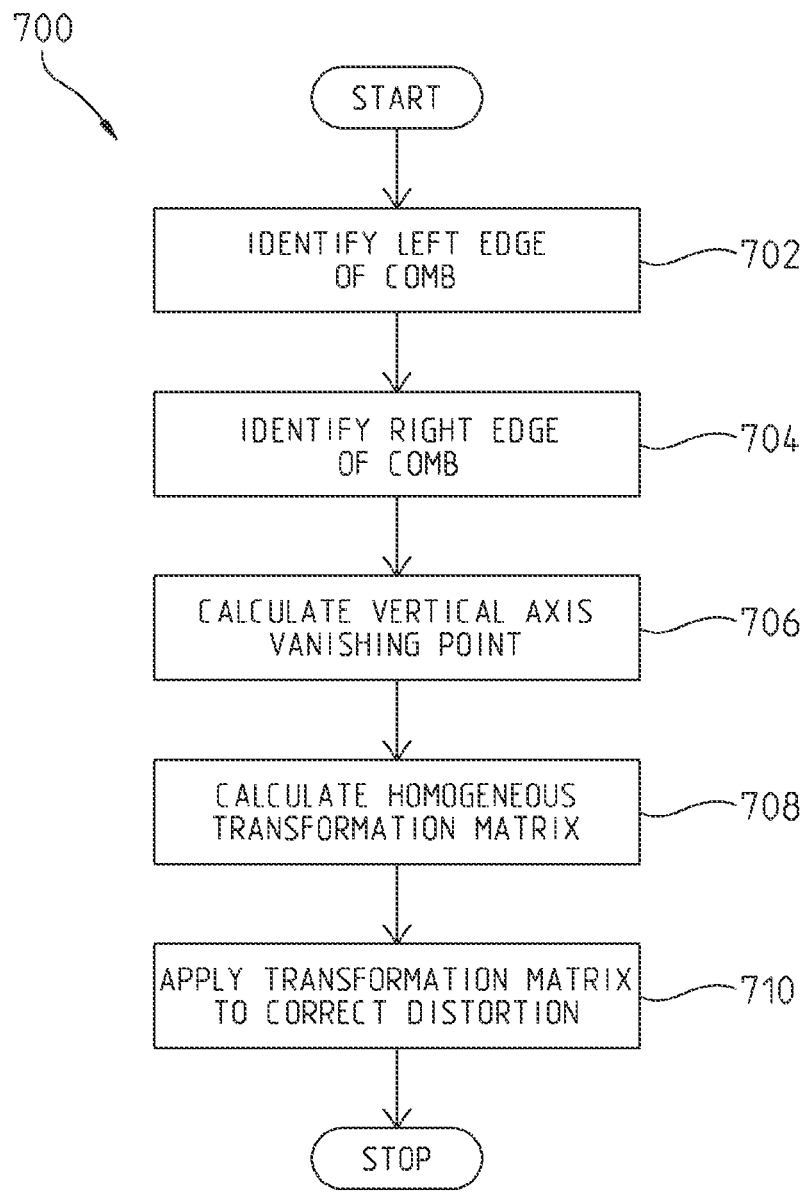
FIG. 23 illustrates an exemplary perspective correction processing sequence of FIG. 20.

As mentioned in connection with block 626 of FIG. 20, image analysis processing sequence 620 corrects for perspective in the stored image. An exemplary processing sequence 700 for correcting for perspective of the comb 120 in the stored image is provided in FIG. 23. The left edge 672 of comb 120 and the right edge 674 of comb 120 are determined, as represented by blocks 702 and 704. These edges are located as described above. Image processing software 214 then determines a vertical axis vanishing point, determines a homogenous transformation matrix, and applies the transformation matrix to correct any distortion or perspective in the stored image, as represented by blocks 706-710. Additional details regarding an exemplary approach to blocks 706-710 are found in an article authored by Fangi et al, titled "PHOTOINTERPRETATION AND SMALL SCALE STEREOPLOTTING WITH DIGITALLY RECTIFIED PHOTOGRAPHS WITH GEOMETRICAL CONSTRAINTS", the contents of which are expressly incorporated by reference herein.

Figure 24A:
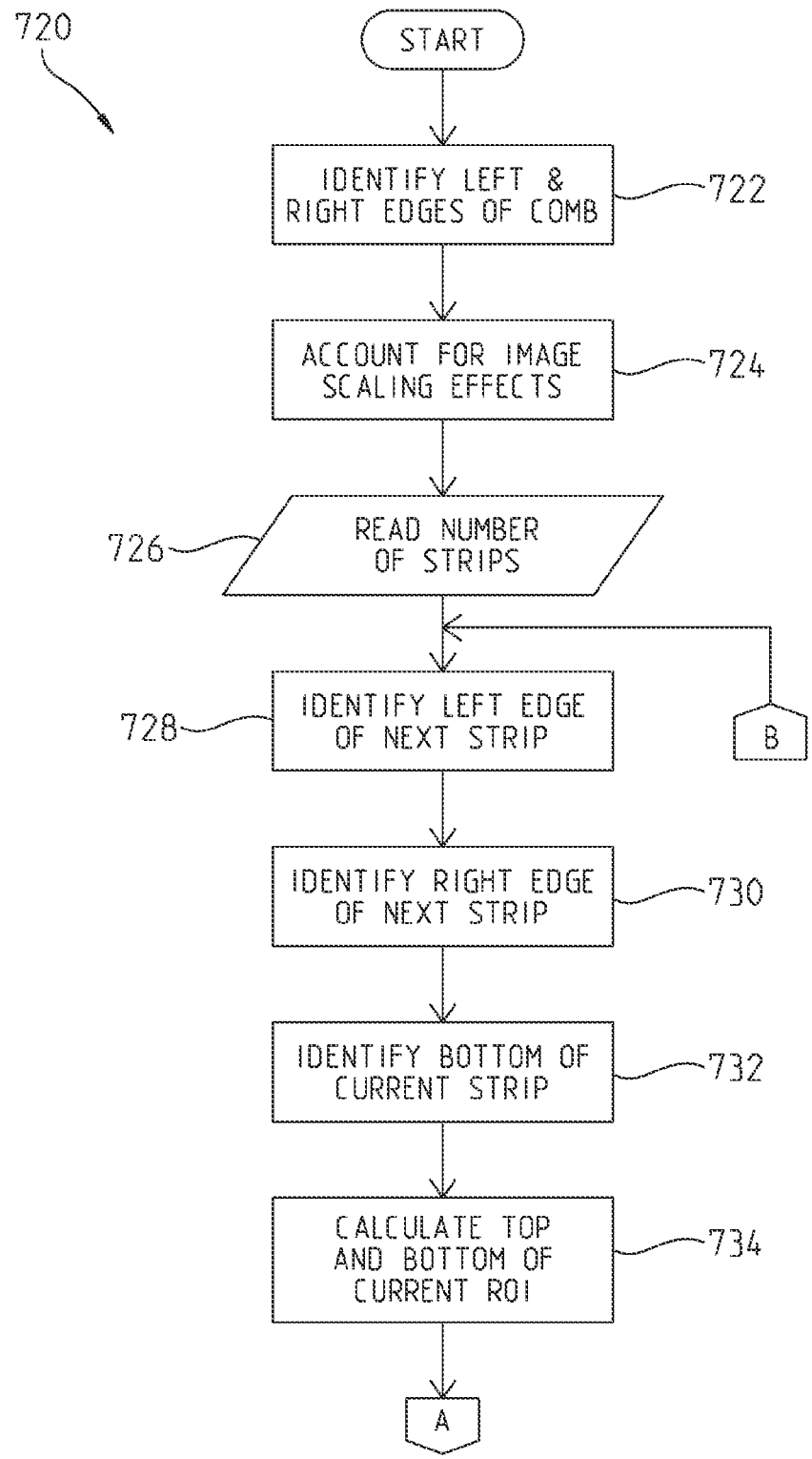
FIGS. 24A and 24B illustrate an exemplary region of interest identification processing sequence of FIG. 20.
Figure 24B:
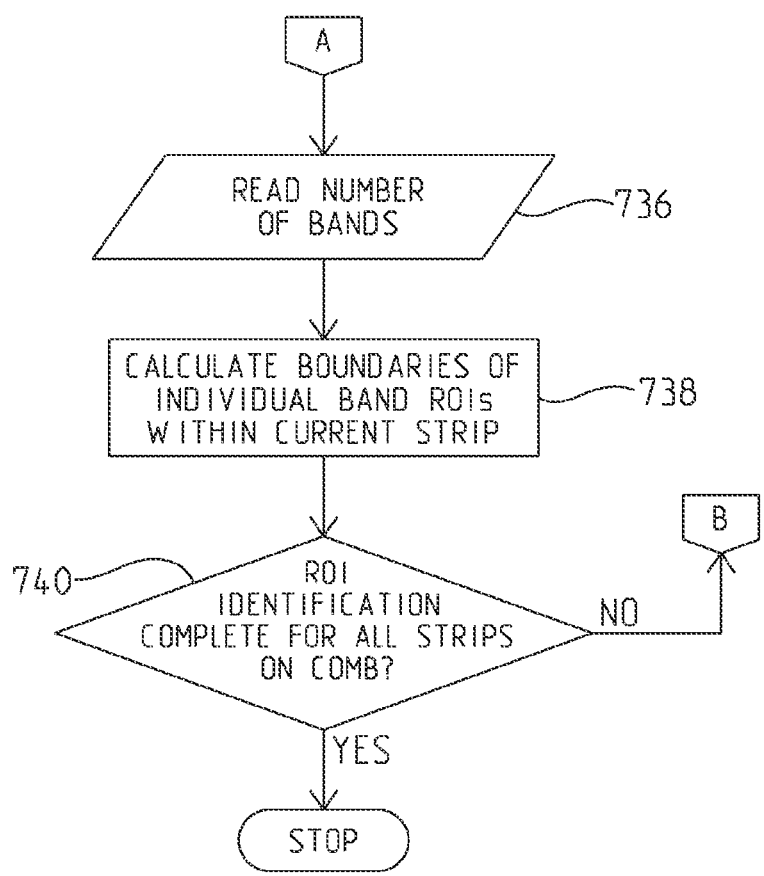

As mentioned in connection with block 628 of FIG. 20, image analysis processing sequence 620 identifies regions of interest for each finger 122 of the comb 120 in the stored image. An exemplary processing sequence 720 for identifying regions of interest for each finger 122 of the comb 120 in the stored image is provided in FIGS. 24A and 24B.

The left and right edges of the comb 120 in the stored image are determined, as represented by block 722. In one embodiment, the left and right edges are found are described above. The separation between the left and right edges of the comb 120 provides a first distance. This distance is compared to a stored known distance for the comb 120 being analyzed. The ratio of the two distances provides a scaling factor for the image of the comb 120. This scaling factor accounts for any image scaling effects, as represented by block 724. Other features of the image of comb 120 may be compared to known quantities to determine a scaling factor.

The number of fingers 122 on the comb 120 is read from settings file 213, as represented by block 726. Image processing software 214 starts at the leftmost pixel of the comb reference row and moves to the right until it encounters a white pixel. This point is identified as the left edge of the leftmost finger, as represented by block 728. Image processing software 214 continues on until it encounters the next edge, which is identified as the right edge of the leftmost finger, as represented by block 730. The separation between the left edge and the right edge of the leftmost finger is scaled by the scaling factor and compared to a known finger width. If the determined value is within a tolerance then the image processing software 214 moves on to block 732. Otherwise, image processing software 214 returns to block 728 and tries another row of the image.

Image processing software 214 determines a location of the bottom of the leftmost finger, as represented by block 732. In one embodiment, image processing software 214 examines all of the pixels between the pixel identified as the left edge and the pixel identified as the right edge and in the same row. If the number of white pixels is above a threshold number, then image processing software 214 moves down one row and examines those pixels. This continues until a row is reached wherein the number of white pixels is below the threshold amount. When this happens the row directly above that row is identified as the bottom row of the finger 122.

Image processing software 214 determines the location of the top and bottom of the region of interest of the leftmost finger 122, as represented by block 734. The location of the top and bottom of the region of interest are known values stored in settings file 213 from the bottom of finger 122. As such, by taking into account the scaling factor and the known values, image processing software 214 is able to determine the top and bottom of the region of interest.

The number of bands in the region of interest are read from settings file 213, as represented by block 726. The location of the bands within the region of interest are known values read from settings file 213. The location of the boundaries of the bands within the region of interest are determined by image processing software 214 by taking into account the scaling factor and the known values. Image processing software 214 determines if the last analyzed finger 122 was the rightmost finger, as represented in block 740. If not control is returned to block 728 and the left edge and the right edge of the next finger 122 are determined. The process continues until all fingers have been analyzed.

While this invention has been described as relative to exemplary designs, the present invention may be further modified within the spirit and scope of this disclosure. Further, this application is intended to cover such departures from the present disclosure as come within known or customary practice in the art to which this invention pertains.

The invention claimed is:

1. A method of analyzing a test strip comb member having a plurality of spaced-apart fingers, each of the fingers having been exposed to a respective plant material and each of the fingers being configured to indicate the presence of one or more plant analytes in the respective plant material, the method comprising:
   capturing an electronic image of the plurality of fingers of the test strip comb member; and
   analyzing the electronic image with an electronic controller to determine if for a first finger of the test strip comb member a first plant analyte is present and for a second finger of the test strip comb member if a second plant analyte is present,
   wherein the electronic image is a color image, each pixel of the color image having a plurality of color values, and the step of analyzing includes the steps of:
   analyzing a first portion of the electronic image corresponding to the first finger;
   determining based on at least one color value of the first portion whether the first plant analyte is bound to the first finger;
   analyzing a second portion of the electronic image corresponding to the second finger; and
   determining based on at least one color value of the second portion whether the second plant analyte is bound to the second finger.

2. The method of claim 1, wherein the first plant analyte is the same as the second plant analyte.

3. The method of claim 1, wherein the step of capturing the electronic image of the plurality of fingers of the test strip comb member includes the steps of:
   monitoring a field of view of a camera;
   detecting a presence of the test strip comb member in the field of view of the camera; and
   storing the electronic image of the plurality of fingers of the test strip comb on a non-transitory computer readable medium when the test strip comb member is detected in the field of view of the camera.

4. The method of claim 3, wherein the step of detecting the presence of the test strip comb member in the field of view of the camera includes the steps of:
   capturing a frame of the camera; and
   analyzing a portion of the captured frame to determine the presence of the test strip comb member.

5. The method of claim 3, wherein the step of analyzing the portion of the captured frame to determine the presence of the test strip comb member includes the steps of: determining an average pixel brightness value for the portion of the captured frame; comparing the average pixel brightness value to a first threshold value;
   determining a number of pixels of the portion of the captured frame whose brightness value exceeds the average brightness value;
   comparing the number of pixels of the portion of the captured frame to a second threshold;
   determining the presence of the test strip comb member when the average pixel brightness exceeds the first threshold and the number of pixels of the portion of the captured frame exceeds the second threshold; and
   storing the captured frame as the electronic image on a non-transitory computer readable medium.

6. The method of claim 1, wherein the step of determining based on at least one color value of the first portion whether the first plant analyte is bound to the first finger includes the steps of:
- for each pixel of the first portion
  - comparing a first color value to a first threshold;
  - comparing a second color value to a second threshold;
  - classifying the pixel as one of indicative of the first analyte being present and indicative of the first analyte being absent based on the comparison of the first color value to the first threshold and the comparison of the second color value to the second threshold;
- determining based on a number of the pixels classified as being indicative of the first analyte being present whether the first analyte is bound to the first finger; and
- wherein the step of determining based on at least one color value of the second portion whether the second plant analyte is bound to the second finger includes the steps of:
- for each pixel of the second portion
  - comparing a first color value to a first threshold;
  - comparing a second color value to a second threshold;
  - classifying the pixel as one of indicative of the second analyte being present and indicative of the second analyte being absent based on the comparison of the first color value to the first threshold and the comparison of the second color value to the second threshold;
- determining based on a number of the pixels classified as being indicative of the second analyte being present whether the second analyte is bound to the second finger.

7. The method according to claim 1, further comprising the step of removing a green bias from the electronic image due to excess plant material in the electronic image.

8. The method according to claim 1, further comprising the step of removing a red bias from the electronic image due to dirt in the electronic image.

9. The method according to claim 1, wherein the electronic image is a color image, each pixel of the color image having a plurality of color values, and the method further comprising the step of color equalizing the electronic image.

10. The method of claim 9, wherein the step of color equalizing the electronic image includes the steps of:
- identifying a respective region of interest for each finger;
- color equalizing the respective region of interest of the first finger; and
- color equalizing the respective region of interest of the second finger independent of the first finger.

11. The method of claim 10, the step of color equalizing the respective region of interest of the first finger includes the steps of:
- scaling a first color value for each pixel of the respective region of interest of the first finger so that the average first color value of all of the pixels of the respective region of interest of the first finger equals a first value; and
- scaling a second color value for each pixel of the respective region of interest of the first finger so that the average second color value of all of the pixels of the respective region of interest of the first finger equals a second value.

12. The method of claim 11, wherein the first value is equal to the second value.

13. The method according to claim 1, wherein the plurality of fingers each include a respective region of interest which includes a plurality of spaced apart band locations and the step of analyzing the electronic image with the electronic controller to determine if for the first finger of the test strip comb member the first plant analyte is present and for the second finger of the test strip comb member if the second plant analyte is present includes the steps of:
- locating the respective region of interest in the electronic image for the first finger and the second finger;
- thresholding the image based on at least one average background intensity of the electronic image; and
- segmenting the electronic image to remove small blobs.

14. The method of claim 13, wherein the step of locating the respective region of interest in the electronic image for the first finger and the second finger includes the steps of:
- determining an orientation of the test strip comb member in the electronic image; deskewing the image such that the first finger and the second finger of the test strip comb member are vertically oriented;
- locating a first reference in the electronic image for the first finger, the first region of interest of the first finger being at a first known position relative to the first reference; and locating a second reference in the electronic image for the second finger, the second region of interest of the second finger being at a second known position relative to the second reference.

15. The method according to claim 13, wherein the step of locating the respective region of interest in the electronic image for the first finger and the second finger further includes the step of correcting the electronic image for perspective distortion.

16. The method according to claim 13, wherein the step of locating the respective region of interest in the electronic image for the first finger and the second finger further includes the step of determining a scaling factor for the electronic image.

17. The method according to claim 13 wherein the step of thresholding the image based on at least one average background intensity includes the steps of:
- determining an average background intensity for a first color value;
- determining an average background intensity for a second color value;
- for each pixel, if one of a value of the pixel for the first color value exceeds the average background intensity for the first color value and a value of the pixel for the second color value exceeds the average background intensity for the second color value then assigning the pixel a third color and otherwise assigning the pixel a fourth color.

18. The method according to claim 1, further comprises the step of storing a qualitative indication of a determination of the presence of the first analyte and a qualitative indication of a determination of the presence of the second analyte.

19. The method according to claim 1, further comprises the step of storing a quantitative indication of a determination of an expression level of the first analyte and a quantitative indication of a determination of an expression level of the second analyte.

20. The method according to claim 1, further comprising the step of providing a closed structure having an opening in a top adapted to permit the test strip comb member to enter an interior of the closed structure and an opening in a bottom adapted to permit the test strip comb member to exit the interior of the closed structure, wherein the step of capturing the electronic image of the plurality of fingers of the test strip comb member occurs while the test strip comb member is positioned in the interior of the closed structure.

21. A system for analyzing a test strip comb having a plurality of spaced-apart fingers, each of the fingers having been exposed to a respective plant material and each of the fingers being configured to indicate the presence of one or more plant analytes in the respective plant material, the system comprising:
- a camera;
- a background member, the test strip comb member being within a field of view of the camera and in front of the background member;
- a light source providing generally uniform illumination of the field of view of the camera; and
- an electronic controller operatively coupled to the camera and configured to analyze an electronic image of the plurality of fingers of the test strip comb member to determine if for a first finger of the test strip comb member a first plant analyte is present and for a second finger of the test strip comb member if a second plant analyte is present,
- wherein the electronic image is a color image, each pixel of the color image having a plurality of color values, and the electronic controller configured to:
- analyze a first portion of the electronic image corresponding to the first finger;
- determinine based on at least one color value of the first portion whether the first plant analyte is bound to the first finger;
- analyze a second portion of the electronic image corresponding to the second finger; and
- determine based on at least one color value of the second portion whether the second plant analyte is bound to the second finger.

22. The system of claim 21, further comprising
a closed structure having an opening in a top adapted to permit the test strip comb member to enter an interior of the closed structure and an opening in a bottom adapted to permit the test strip comb member to exit the interior of the closed structure, the electronic image of the plurality of fingers of the test strip comb member being captured while the test strip comb member is positioned in the interior of the closed structure.

23. The system of claim 22, wherein the background member is a removable plate which provides a contrasting background relative to the test strip comb member.

24. The system of claim 21, further comprising a conveyor system having a transport member upon which the test strip comb member is supported, wherein the electronic controller is operatively coupled to a drive system of the conveyor system.

25. The system of claim 24, wherein the background member is the transport member of the conveyor system.

26. The system of claim 24, further comprising a cleaning system to remove excess plant debris from the transport member.

27. The system of claim 24, further comprising a feeder system which places the test strip comb member on the conveyor system.

28. The system of claim 27, wherein the feeder system places the test strip comb member onto transport member with a generally uniform spacing relative to a prior test strip comb member and a subsequent test strip comb member.

29. The system of claim 21, further comprising
a display device which displays a user interface comprising
a first region which displays the electronic image of the test strip comb member;
a second region which displays an indicator providing an indication to the operator of when the electronic controller is ready to analyze a second test strip comb member.

30. The system of claim 29, wherein a set number of test strip comb members are to be analyzed and the user interface provides an indication with the display device of a number of test strip members that have been analyzed.

* * * * *